(12) United States Patent
Wolfinbarger, Jr. et al.

(10) Patent No.: US 9,936,688 B2
(45) Date of Patent: *Apr. 10, 2018

(54) PROCESS FOR DEVITALIZING SOFT-TISSUE ENGINEERED MEDICAL IMPLANTS, AND DEVITALIZED SOFT-TISSUE MEDICAL IMPLANTS PRODUCED

(71) Applicant: LifeNet Health, Virgina Beach, VA (US)

(72) Inventors: Lloyd Wolfinbarger, Jr., Norfolk, VA (US); Perry Lange, Virginia Beach, VA (US); Alyce Linthurst-Jones, Virginia Beach, VA (US); Eric Moore, Virginia Beach, VA (US); Barry Nolf, Courtland, VA (US)

(73) Assignee: LifeNet Health, Virginia Beach, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/058,240

(22) Filed: Oct. 19, 2013

(65) Prior Publication Data

US 2014/0154663 A1    Jun. 5, 2014

Related U.S. Application Data

(63) Continuation of application No. 10/694,190, filed on Oct. 28, 2003, now Pat. No. 8,563,232, which is a continuation-in-part of application No. 09/660,422, filed on Sep. 12, 2000, now Pat. No. 6,743,574.

(51) Int. Cl.
| | | |
|---|---|---|
| *A01N 1/00* | (2006.01) | |
| *A01N 1/02* | (2006.01) | |
| *A61L 27/36* | (2006.01) | |
| *C12N 5/00* | (2006.01) | |
| *A61K 35/12* | (2015.01) | |

(52) U.S. Cl.
CPC ............ *A01N 1/0247* (2013.01); *A01N 1/00* (2013.01); *A01N 1/02* (2013.01); *A01N 1/0226* (2013.01); *A61L 27/3604* (2013.01); *A61L 27/3683* (2013.01); *A61L 27/3691* (2013.01); *C12N 5/00* (2013.01); *A61K 35/12* (2013.01); *C12N 2509/00* (2013.01)

(58) Field of Classification Search
CPC ...................................................... A01N 1/02
See application file for complete search history.

(56) References Cited

U.S. PATENT DOCUMENTS

| | | |
|---|---|---|
| 3,458,397 A | 7/1969 | Myers et al. |
| 4,278,701 A | 7/1981 | Von Hagens |
| 4,357,274 A | 11/1982 | Werner |
| 4,372,888 A | 2/1983 | Hjelmeland |
| 4,394,370 A | 7/1983 | Jefferies |
| 4,539,716 A | 9/1985 | Bell |
| 4,546,500 A | 10/1985 | Bell |
| 4,553,974 A | 11/1985 | Dewamkee |
| 4,678,470 A | 7/1987 | Nashef et al. |
| 4,776,853 A | 10/1988 | Klement et al. |
| 4,801,299 A | 1/1989 | Brendel et al. |
| 4,835,102 A | 5/1989 | Bell et al. |
| 4,846,835 A | 7/1989 | Grande |
| 4,950,296 A | 8/1990 | McIntyre |
| 4,969,912 A | 11/1990 | Kelman et al. |
| 5,061,286 A | 10/1991 | Lyle |
| 5,095,925 A | 3/1992 | Elledge et al. |
| 5,116,552 A | 5/1992 | Morita et al. |
| 5,118,512 A | 6/1992 | O'Leary et al. |
| 5,120,833 A | 6/1992 | Kaplan |

(Continued)

FOREIGN PATENT DOCUMENTS

| | | |
|---|---|---|
| DE | 19513177 A1 | 10/1996 |
| SU | 1175481 A1 | 8/1985 |

(Continued)

OTHER PUBLICATIONS

Balderson et al., 45th Annual Meeting, Orthopaedic Research Society. (Feb. 1-4, 1999), pp. 785.
H.-H. Sievers, et al., "Decellularized pulmonary homograft (SynerGraft) for reconstruction of the right ventricular outflow tract: first clinical experience" Z. Kardiol, vol. 92, No. 53, 2003.
Robert Madden, et al., "Decellularized Cadaver Vein Allografts Used for Hemodialysis Access Do Not Cause Allosensitization or Preclude Kidney Transplanation" Journal of Kidney Diseases, vol. 40, No. 6, Dec. 2002, pp. 1240-1243.

(Continued)

Primary Examiner — Allison M Fox
(74) Attorney, Agent, or Firm — RatnerPrestia

(57) ABSTRACT

The invention provides methodologies and apparatus for producing devitalized soft-tissue implants where the implant retains metabolically non-viable and/or reproductively non-viable cells, and preferably retains large molecular weight cytoplasmic proteins, such implants produced both in small quantities and in commercializable quantities. Such soft-tissue implants include vascular graft substitutes. A devitalized graft is produced by subjecting the tissue sample to an induced pressure mediated flow of an extracting solution, optionally followed by inducing a pressure mediated flow of a salt solution, then washing the tissue to produce the devitalized graft. The devitalized grafts produced are uniform and non-immunogenic. The inventive method allows for the production of multiple devitalized soft tissue implants, where processing time is significantly less than prior art processes and the number of implants produced per day is increased over prior art processes. In clinical use, the devitalized grafts produced exhibit significantly improved in long-term durability and function, and enhanced recellularization post-implantation.

10 Claims, 4 Drawing Sheets

(56) References Cited

U.S. PATENT DOCUMENTS

| | | | |
|---|---|---|---|
| 5,131,907 A | 7/1992 | Williams et al. | |
| 5,171,273 A | 12/1992 | Silver et al. | |
| 5,290,558 A | 3/1994 | O'Leary et al. | |
| 5,298,254 A | 3/1994 | Prewett et al. | |
| 5,333,626 A | 8/1994 | Morse et al. | |
| 5,336,616 A | 8/1994 | Livesey et al. | |
| 5,352,463 A | 10/1994 | Badylak et al. | |
| 5,357,636 A | 10/1994 | Dresdner, Jr. et al. | |
| 5,397,353 A | 3/1995 | Oliver et al. | |
| 5,432,712 A | 7/1995 | Chan | |
| 5,466,462 A | 11/1995 | Rosenthal et al. | |
| 5,507,813 A | 4/1996 | Dowd et al. | |
| 5,513,662 A | 5/1996 | Morse et al. | |
| 5,525,646 A | 6/1996 | Lundgren et al. | |
| 5,531,791 A | 7/1996 | Wolfinbarger, Jr. | |
| 5,556,379 A | 9/1996 | Wolfinbarger | |
| 5,558,875 A | 9/1996 | Wang | |
| 5,607,476 A | 3/1997 | Prewett et al. | |
| 5,613,982 A | 3/1997 | Goldstein | |
| 5,624,463 A | 4/1997 | Stone et al. | |
| 5,632,778 A | 5/1997 | Goldstein | |
| 5,702,446 A | 12/1997 | Schenck et al. | |
| 5,716,405 A | 2/1998 | Mittelman | |
| 5,718,012 A | 2/1998 | Cavallaro | |
| 5,720,777 A | 2/1998 | Jaffe et al. | |
| 5,762,600 A | 6/1998 | Bruchman et al. | |
| 5,772,439 A | 6/1998 | Yamaoka et al. | |
| 5,792,603 A | 8/1998 | Dunkelman et al. | |
| 5,797,871 A | 8/1998 | Wolfinbarger, Jr. | |
| 5,820,581 A | 10/1998 | Wolfinbarger, Jr. | |
| 5,843,180 A | 12/1998 | Jaffe et al. | |
| 5,843,181 A | 12/1998 | Jaffe et al. | |
| 5,843,182 A | 12/1998 | Goldstein | |
| 5,855,610 A | 1/1999 | Vacanti et al. | |
| 5,855,617 A | 1/1999 | Orton | |
| 5,855,620 A | 1/1999 | Bishopric et al. | |
| 5,856,367 A | 1/1999 | Barrows et al. | |
| 5,863,531 A | 1/1999 | Naughton et al. | |
| 5,879,876 A | 3/1999 | Wolfinbarger, Jr. et al. | |
| 5,885,617 A | 3/1999 | Jordan | |
| 5,899,936 A | 5/1999 | Goldstein | |
| 5,899,939 A | 5/1999 | Boyce et al. | |
| 5,916,266 A | 6/1999 | Yui et al. | |
| 5,928,945 A | 7/1999 | Seliktar | |
| 5,944,755 A | 8/1999 | Stone | |
| 5,976,104 A | 11/1999 | Wolfinbarger, Jr. | |
| 5,977,034 A | 11/1999 | Wolfinbarger, Jr. | |
| 5,977,432 A | 11/1999 | Wolfinbarger, Jr. | |
| 5,993,844 A | 11/1999 | Abraham et al. | |
| 5,997,896 A | 12/1999 | Carr, Jr. et al. | |
| 6,024,735 A | 2/2000 | Wolfinbarger, Jr. | |
| 6,030,635 A | 2/2000 | Gertzman et al. | |
| 6,039,762 A | 3/2000 | McKay | |
| 6,046,379 A | 4/2000 | Stone et al. | |
| 6,060,306 A | 5/2000 | Flatt et al. | |
| 6,110,206 A | 8/2000 | Stone | |
| 6,110,209 A | 8/2000 | Stone | |
| 6,121,042 A | 9/2000 | Peterson et al. | |
| 6,123,731 A | 9/2000 | Boyce et al. | |
| 6,162,258 A | 12/2000 | Scarborough et al. | |
| 6,179,872 B1 | 1/2001 | Bell et al. | |
| 6,200,347 B1 | 3/2001 | Anderson et al. | |
| 6,214,054 B1 | 4/2001 | Cunanan et al. | |
| 6,241,771 B1 | 6/2001 | Gresser et al. | |
| 6,255,925 B1 * | 7/2001 | DiMarco et al. | ... A61L 27/3604 |
| 6,277,555 B1 | 8/2001 | Duran et al. | |
| 6,293,970 B1 | 9/2001 | Wolfinbarger, Jr. | |
| 6,294,041 B1 | 9/2001 | Boyce et al. | |
| 6,294,187 B1 | 9/2001 | Boyce et al. | |
| 6,312,474 B1 | 11/2001 | Francis et al. | |
| 6,340,477 B1 | 1/2002 | Anderson | |
| 6,348,069 B1 | 2/2002 | Vacanti et al. | |
| 6,352,708 B1 | 3/2002 | Duran et al. | |
| 6,371,992 B1 | 4/2002 | Tanagho et al. | |
| 6,376,244 B1 | 4/2002 | Atala | |
| 6,379,367 B1 | 4/2002 | Vibe-Hansen et al. | |
| 6,379,385 B1 | 4/2002 | Kalas et al. | |
| 6,398,811 B1 | 6/2002 | McKay | |
| 6,416,995 B1 | 7/2002 | Wolfinbarger | |
| 6,428,802 B1 | 8/2002 | Atala | |
| 6,432,710 B1 | 8/2002 | Boss, Jr. et al. | |
| 6,432,712 B1 | 8/2002 | Wolfinbarger, Jr. | |
| 6,436,138 B1 | 8/2002 | Dowd et al. | |
| 6,437,018 B1 | 8/2002 | Gertzman et al. | |
| 6,448,076 B2 | 9/2002 | Dennis et al. | |
| 6,451,543 B1 | 9/2002 | Kochendoerfer et al. | |
| 6,454,804 B1 | 9/2002 | Ferree | |
| 6,454,811 B1 | 9/2002 | Sherwood et al. | |
| 6,458,158 B1 | 10/2002 | Anderson et al. | |
| 6,479,064 B1 | 11/2002 | Atala | |
| 6,482,584 B1 | 11/2002 | Mills et al. | |
| 6,488,033 B1 | 12/2002 | Cerundolo | |
| 6,506,386 B1 | 1/2003 | Friede et al. | |
| 6,544,289 B2 | 4/2003 | Wolfinbarger, Jr. | |
| 6,548,297 B1 | 4/2003 | Kuri-Harcuch et al. | |
| 6,569,200 B2 | 5/2003 | Wolfinbarger, Jr. | |
| 6,582,696 B2 | 6/2003 | Kuri-Harcuch et al. | |
| 6,630,001 B2 | 10/2003 | Duran et al. | |
| 6,648,919 B2 | 11/2003 | Ferree | |
| 6,652,818 B1 | 11/2003 | Mills et al. | |
| 6,734,018 B2 | 5/2004 | Wolfinbarger, Jr. | |
| 6,743,574 B1 | 6/2004 | Wolfinbarger, Jr. | |
| 6,780,510 B2 | 8/2004 | Ogle et al. | |
| 6,783,556 B1 | 8/2004 | Gabay | |
| 6,855,169 B2 | 2/2005 | Boyer, II et al. | |
| 6,858,042 B2 | 2/2005 | Nadler et al. | |
| 6,872,357 B1 | 3/2005 | Bronshtein et al. | |
| 6,902,578 B1 | 6/2005 | Anderson et al. | |
| 6,911,212 B2 | 6/2005 | Gertzman et al. | |
| 6,936,271 B1 | 8/2005 | Oliver et al. | |
| 6,942,961 B1 | 9/2005 | Baumgartner | |
| 6,958,149 B2 | 10/2005 | Vukicevic et al. | |
| 6,962,775 B2 | 11/2005 | Kuri-Harcuch et al. | |
| 6,998,135 B1 | 2/2006 | Sunwoo et al. | |
| 7,063,726 B2 | 6/2006 | Crouch et al. | |
| 7,067,123 B2 | 6/2006 | Gomes et al. | |
| 7,108,721 B2 | 9/2006 | Huckle et al. | |
| 7,122,057 B2 | 10/2006 | Beam et al. | |
| 7,157,428 B2 | 1/2007 | Kusanagi et al. | |
| 2001/0004715 A1 | 6/2001 | Duran et al. | |
| 2001/0049138 A1 | 12/2001 | Cheung | |
| 2001/0055809 A1 | 12/2001 | Mangat | |
| 2002/0012982 A1 | 1/2002 | Blakesley et al. | |
| 2002/0106625 A1 | 8/2002 | Hung et al. | |
| 2002/0115208 A1 | 8/2002 | Mitchell et al. | |
| 2002/0192191 A1 | 12/2002 | Kuri-Harcuch et al. | |
| 2002/0192197 A1 | 12/2002 | Kuri-Harcuch et al. | |
| 2003/0068416 A1 | 4/2003 | Burgess et al. | |
| 2003/0083752 A1 | 5/2003 | Wolfinbarger, Jr. et al. | |
| 2003/0087428 A1 | 5/2003 | Wolfinbarger, Jr. et al. | |
| 2003/0130746 A1 | 7/2003 | Ashworth et al. | |
| 2003/0135284 A1 | 7/2003 | Crouch et al. | |
| 2003/0143207 A1 | 7/2003 | Livesey et al. | |
| 2003/0185702 A1 | 10/2003 | Burgess et al. | |
| 2003/0217415 A1 | 11/2003 | Crouch et al. | |
| 2003/0219417 A1 | 11/2003 | Wolfinbarger, Jr. | |
| 2004/0037735 A1 | 2/2004 | DePaula et al. | |
| 2004/0057936 A1 | 3/2004 | Cheung | |
| 2004/0059364 A1 | 3/2004 | Gaskins et al. | |
| 2004/0059430 A1 | 3/2004 | Kim et al. | |
| 2004/0067582 A1 | 4/2004 | Wolfinbarger, Jr. et al. | |
| 2004/0076657 A1 | 4/2004 | Wolfinbarger, Jr. et al. | |
| 2004/0219058 A1 | 11/2004 | Shimp et al. | |
| 2004/0219182 A1 | 11/2004 | Gomes et al. | |
| 2004/0219659 A1 | 11/2004 | Altman et al. | |
| 2004/0230303 A1 | 11/2004 | Gomes et al. | |
| 2005/0019865 A1 | 1/2005 | Kihm et al. | |
| 2005/0028228 A1 | 2/2005 | McQuillan et al. | |
| 2005/0064042 A1 | 3/2005 | Vunjak-Novakovic et al. | |
| 2005/0112086 A1 | 5/2005 | Swan et al. | |
| 2005/0152987 A1 | 7/2005 | Malinin et al. | |
| 2005/0196460 A1 | 9/2005 | Malinin | |
| 2005/0209705 A1 | 9/2005 | Niederauer et al. | |
| 2005/0251268 A1 | 11/2005 | Truncale | |

(56) References Cited

U.S. PATENT DOCUMENTS

| | | |
|---|---|---|
| 2006/0073592 A1 | 4/2006 | Sun et al. |
| 2006/0074466 A1 | 4/2006 | Malinin |
| 2006/0173394 A1 | 8/2006 | Stroock et al. |
| 2006/0247790 A1 | 11/2006 | McKay |
| 2007/0038299 A1 | 2/2007 | Stone et al. |
| 2007/0082057 A1 | 4/2007 | Masinaei et al. |
| 2007/0082058 A1 | 4/2007 | Masinaei et al. |
| 2007/0083270 A1 | 4/2007 | Masinaei et al. |
| 2007/0093896 A1 | 4/2007 | Malinin |
| 2007/0098759 A1 | 5/2007 | Malinin |
| 2007/0135917 A1 | 6/2007 | Malinin |
| 2007/0135918 A1 | 6/2007 | Malinin |
| 2007/0135928 A1 | 6/2007 | Malinin |
| 2007/0149982 A1 | 6/2007 | Lyons |
| 2007/0233272 A1 | 10/2007 | Boyce et al. |
| 2007/0276506 A1 | 11/2007 | Troxel |
| 2007/0292401 A1 | 12/2007 | Harmon et al. |
| 2008/0255676 A1 | 10/2008 | Semler et al. |
| 2008/0262616 A1 | 10/2008 | McKay |
| 2009/0076606 A1 | 3/2009 | Huerta et al. |
| 2013/0023721 A1 | 1/2013 | Matheny |

FOREIGN PATENT DOCUMENTS

| | | |
|---|---|---|
| WO | WO 96/14738 | 5/1996 |
| WO | WO 98/07452 | 2/1998 |
| WO | WO 01/13971 A1 | 3/2001 |
| WO | WO 2005/009134 A1 | 2/2005 |
| WO | WO 2006/090372 A1 | 8/2006 |

OTHER PUBLICATIONS

P.M. Dohmen, et al., "In Vitro hydrodynamics of a decellularized pulmonary procine valve, compared with a glutarldehyde and polyurethane heart valve" Journal of Artificial Organs, vol. 25, No. 11, 2002, pp. 1089-1094.

B. S. Conklin, et al., "Development and evaluation of a novel decellularized vascular xenograft" Medical Engineering and Physics, vol. 24, 2002, pp. 173-183.

J. Clark, et al., "Decellularized Dermal Grafting in Cleft Palate Repair" Facial Plastic Surg., vol. 5, 2003, pp. 40-44.

Ronald C. Elkins, et al.. "Decellularized Human Valve Allofgrafts" Society of Thoracic Surgeons, 2001, pp. S428-S432.

Steven Goldstein, et al., "Transpecies Heart Valve Transplant: Advanced Studies of a Bioengineered Xeno-Autograft" Society of Thoracic Surgeons, 2000, pp. 1963-1969.

Pascal M. Dohmen, et al., "Ross Operation with a Tissue-Engineered Heart Valve" Society of Thoracic Surgeons, 2002, pp. 1438-1442.

David W. Courtman, et al., "Biomechanical and ultrastructural comparison of cryopreservation and a novel cellular extraction of porcine aortic valve leaflets". Journal of Biomedical Materials Research, vol. 29. 1995, pp. 1507-1516.

Gregory Wilson, et al., "Acellular Matrix Allograft Small Caliber Vascular Prostheses" Trans. Am. Sog. Artif. Intern. Organs, 1990, vol. XXXVI, pp. M340-M343.

David W. Courtman, et al., "The Acellular Matrix Vascular Prosthesis: Investigation of its Potential as a Xenograft for Clinical Application" Biomaterial Tissue Interfaces, vol. 10, 1992, pp. 241-246.

David W. Courtman, et al., "Development of a pericardial acellular matrix biomaterial: Biochemical and mechanical effects of cell extraction" Journal of Biomedical Materials Research, vol. 28, 1994, pp. 655-566.

Gregory J. Wilson, et al., "Acellular Matrix: A Biomaterials Approach for Coronary Artery Bypass and Heart Valve Replacement" Society of Thoracic Surgeons, 1995, pp. 5353-5358.

Satiris A. Korrossis, et al., "Tissue Engineering of Cardiac Valve Prostheses II: Biomechanical Characterization of Decellularized Porcine. Aortic Heart Valves" Heart Valve Disease, vol. 11, No. 4, Jul. 2002, pp. 463-471.

Lalka et al., "Acellular vascular matrix: a natural endothelial cell substrate" (1989) Annals of Vascular Surgery, vol. 3, No. 2, pp. 108-117.

Bianchi et al., 21st. Annual Meeting. American Association of Tissue Banks. (Aug. 23-27, 1997), p. 48.

Kang et al., "The biomechanical properties of deep freezing and freeze drying bones and their biomechanical changes after in-vivo allograft," Yonsei Medical Journal. vol. 36, No. 4, (1995), pp. 332-335.

Voggenreiter et al.. "Effects of preservation and sterilization on cortical bone grafts. A scanning electron microscopic study," Archives of Orthopaedic and Traumatic Surgery, vol. 113. (1994). pp. 294-296.

Pelker, et al., "Biomechanical properties of bone autografts and allografts," Orthopedic Clinics of North America, vol. 18, No. 2, (Apr. 1987), pp. 235-239.

Pelker, et al., "Effects of freezing and freeze-drying on the biomechanical properties of rat bone." Journal of Orthopaedic Research, vol. 1, No. 4, (1984), pp. 405-411.

Pelker, et al., "Biomechanical properties of bone allografts," Clinical Orthopaedics and Related Research, No. 174. (Apr. 1983), pp. 54-57.

Triantafyliou et al., "The mechanical properties of the lyophilized and irradiated bone grafts" Acta athopaedica BelQica, vol. 41, Suppl. I. (1975), pp. 35-44.

Jerosch et al., "Effects of various rehydration periods on the stability and water content of bone transplants following freeze-drying, gamma sterilization and lipid extraction" Zeitschrift Orthopadie 132. (1994), pp. 335-341.

Pappas, A .• Cryobiology. vol. 4. No. 6 (1968), pp. 358-375.

Boyne, P. "Review of the literature on cryopreservation of bone" Cryobiology. vol. 4, No. 6 (1968), pp. 341-357.

Kreuz, F., et al .• "The Preservation and Clinical Use of Freeze Dried Bone," J Bone Joint Surg. 1951; 33A; 863.

Schwade, N., "Implants, Soft Tissue, Alloderm," emedicine.com, copyright 2004.

Wolfinbarger, L., Zhang. YI, Adam, BLT., Hornsi, D., Gates, K., and Sutherland, V .• 1994, Biomechanical aspects on rehydrated freeze-dried human allograft dura mater tissues• J. Applied biomaterials, 5:265-270.

"RPMI 1640", Jostin Diabetes Center, JoslinResearch.org, Retrieved Sep. 9, 2009 <http://www.joslinresearch.org/medianet/Reagent.sub.--Contents.sub.--D- etail.asp?Item.sub.--ID=1>.

Non Final Office Action for U.S. Appl. No. 12/404,855, dated Jun. 22, 2016, 16 pages.

Final Office Action for U.S. Appl. No. 11/826,522, dated Oct. 11, 2016, 19 pages.

Office Action for U.S. Appl. No. 14/776,153 dated Oct. 11, 2016, 11 pages.

Communication pursuant to Art. 94(3) for European Patent Application No. 08780196.5 dated Dec. 23, 2016.

Non Final Office Action for U.S. Appl. No. 13/537,194, dated Oct. 31, 2016, 30 pages.

Abstract of Atkins, TW, "Fabrication of Microspheres Using Blends of Poly(Ethylene Adipate) and Poly(Ethylene Adipate)/Poly(Hydroxybutyrate-Hydroxyvalerate) with Poly(Caprolactone): Incorporation and Release of Bovine Serum Albumin,"J Biomater Sci Polym Ed. 1997, vol. 8, No. 11, pp. 833-845.

Abstract of Aidulis et al., Processing of ovine cardiac allografts: 1. Effects of preservation method on structure and mechanical properties, Cell and Tissue Banking, (2002), vol. 3, No. 2, pp. 79-89.

Abstract of Bertuzzi et al, "Sebacic Acid Binding to Human Plasma Albumin," Biochem Pharmacol, (1993), vol. 45, pp. 697-702.

Abstract of Bodnar, E., et al., "Long Term Performance of 580 Homograft and Autograft Valves Used for Aortic Valve Replacement," Thorac Cardiovasc Surg., Feb. 1979, pp. 31-38, vol. 27, No. 1.

Abstract of Boogaard, PJ, et al., "Effects of Exposure to Low Concentrations of Chlorinated Hydrocarbons on the Kidney and Liver of Industrial Workers," Br J Ind Med, Apr. 1993, vol. 50, pp. 331-339.

(56) References Cited

OTHER PUBLICATIONS

Abstract of Bourroul et al., "Sterilization of Skin Allografts by Ionizing Radiation," Cell Mol Biol, 2002, pp. 803-807, vol. 48, No. 7.

Abstract of Chang, CM, et al., "Swelling of and Drug Release from Monoglyceride-Based Drug Delivery Systems," J. Pharm. Sci. Jun. 1997, pp. 747-752.vol. 86.

Abstract of Pessoa De Barron, TE, et al., "Plasty of Tendon with Dura Mater. Experimental Study," Arch Orthop Trauma Surg. 1990, vol. 109, pp. 131-132.

Abstract of Derwin, KA, et al., Commercial Extracellular Matriz Scaffolds for Rotator Cuff Tendon Repair, Biomechanical, Biochemical, and Cellular Properties, J Bone Joint Surg Am ., Dec. 2006, pp. 2665-2672, vol. 88.

Abstract of Duncan-Hewitt, WC., et al., "Modeling the Unixial Compaction of Pharmaceutical Powders Using the Mechanical Properties of Single Crystals, II: Brittle Materials," J Pharm Sci, Mar. 1990, vol. 79, pp. 273-276.

Abstract of Ema, M., et al., "Comparative Developmental Toxicity of n-butyll Benzyl Phithalate and di-n-butyl Phihalate in Rats," Arch Environ Contam Toxicol, Feb. 1995, pp. 223-228, vol. 28.

Abstract of Ensikat, HJ, et al., Liquid Substitution: A Versatile Procedure for SEM Specimen Preparation of Biological Materials Without Drying or Coating, J. Microsc. Dec. 1993,.vol. 172, Pt. 3, pp. 195-203.

Abstract of Frangos, SA, et al., "Chlorinated Hydrocarbon J Solvents: Substituting Our Way Toward Human Carcinogenicity," Am J Ind Med, Oct. 1993, pp. 355-364, vol. 24.

Abstract of Fries, KM., et al. "31P NMR and Chloride Ion Kinetics of Alkylating Minoester Phophoramidates,"J Med Chem, Feb. 1991, vol. 34, pp. 565-569.

Abstract of Ghosh, MM, et al., "A Comparison of Methodologies for the Preparation of Human Epidermal-Dermal Composites," Ann Plast. Surg., Oct. 1997, pp. 390-404, vol. 39.

Abstract of Graham, BS, et al., "An In Vivo and in Vitro Study of the Loss of Plasticizer from Scott Polymer-Gel Materials," J. Dent Res. May 1991, vol. 70, No. 5, pp. 870-873.

Abstract of Greco, AV, et al., "Toxicity of Disodium Sebacate," Drugs Exp. Clin Res, 1990, pp. 531-536, vol. 16.

Abstract of Harsanyi et al., "Hamster Cheek-Pouch Testing of Dental Soft Polymers," J. Dent. Res., 1991, vol. 70, pp. 991-996.

Abstract of Hinton, R. et al., "A Biomechanical Analysis of Solvent-Dehydrated and Freeze-Dried Human Fascia Lata Altografts. A Preliminary Report," Am J Sports Med. Sep.-Oct. 1992, vol. 20, pp. 607-612.

Abstract of Ingegneri, A., et al., "An 11-Year Assessment of 93 Flash-Frozen Homograft Valves in the Aortic Position," Thorac Cardiovasc Surg. Oct. 1979, pp. 304-307, vol. 27, No. 5.

Kabasawa, Y., et al., "Allergic Contact Dermatitis from Ethyl Sebacate," Contact Dermatitis, Apr. 1990, vol. 22, p. 226. El.

Abstract of Kiyosawa, K., et al., "Volumetric Properties of Polyols (Ethylene Glycol, Glycerol, Meso-Erythritol, Xylitol, and Mannitol) in Relation to Their Membrane Permeability: Group Additivity and Estimation of the Maximum Radius of Their Molecules," Biochim Biophys Acta, May 7, 1991, vol. 1064, pp. 252-255.

Abstract of McCarty, LP, et al., "Acute toxicity in rats of chlorinated hydrocarbons given via the intratracheal route", Hum Exp Toxicol, May 1992, vol. 11, pp. 173-177.

Abstract of Meintjes, J., et al. "Synthetic Biological and Composite Scaffolds for Abdominal Wall Reconstruction," Expert Rev Med Devices, Mar. 2011, pp. 275-288, vol. 8, No. 2.

Abstract of Mingrone, G., et al., "Kinetics and Thermogenesis of Medium-Chained Monocarboxlyic and Dicarboxylic Acids in Man: Sebacate and Medium-Chain Triglycerides," JPEN J Parenter Enteral Nutr, May-Jun. 1993, pp. 257-264, vol. 17.

Abstract of Mingrone, G., et al., "Tissue Uptake and Oxidation of Disdoium Sebacate in Man," JPEN J Parenter Enteral Nutr, Jul.-Aug. 1991, vol. 15, pp. 454-459.

Mochida, K., et al., "Acetyl Tributyl Citrate and Dibutyl Sebacate Inhibit the Growth or Cultured Mammalian Cells," Bull Environ Contains Toxicol, Apr. 1996, vol. 56, pp. 635-637.

Abstract of Moore, CH, et al., "Analysis of Homograft Valve Failure in 311 Patients Followed Up to 10 Years," Ann Thorac Surg. Sep. 1975, pp. 274-281, vol. 20, No. 3.

Abstract of Moser, Ju., et al., "Aliphatic and Heterocyclic Relationships of Mono-and Bivalent Ligands at Muscarinic Analogues of Arecaidine Propargyl Ester. Structure-Activity M1(M4), M2 and M3 Receptor Subtypes," Arzneimittelforschung, Apr. 1995, vol. 45, pp. 449-455.

Abstract of Ng, KW, et al., "In Vitro Characterization of Natural and Synthetic Dermal Matrices Cultured with Human Derman Fibroblasts," Biomaterials, Jun. 2004, pp. 2807-2818, vol. 25, No. 14.

Abstract of Nishinari, K., et al., "Effect of Sugards and Polyols on Water in Agarose Geis," Adv Exp Med Biol. 1991, vol. 302, pp. 235-249.

Abstract of Norling et al., "Formulation of a Drug Delivery System Based on a Mixture of Monoglycerides and Triglycerides for Use in the treatment of Peridonta; Disease," J Clin Periodontal, Oct. 1992, pp. 687-692, vol. 19.

Abstract of Parker et al., "Elasticity of Frozen Aortic Valve Homografts," Cardiovasc Res. 1977, pp. 156-159, vol. 11, No. 2.

Abstract of Petschow, B.W. et al., "Susceptibility of Helicobacter Pylori to Bactericidal Properties of Medium-Chain Monoglycerides and Free Fatty Acids," Antimicrob Agents Chemother, Feb. 1996, vol. 40, pp. 302-306.

Abstract of Reddy, VN., et al., "Study of Polyol Pathway and Cell Permeability Changes in Human Lens and Retinal Pigment Epithelium in Tissue Culture", Invest Opthalmol Vis Sci, Jun. 1992, vol. 33, pp. 2334-2339.

Abstract of Ross, "Connective tissue cells, cell proliferation and synthesis of extracellular matrix-a-review", Philosophical Transactions Royal Society London B Bio Sci., Jul. 1975: vol. 271(912): pp. 247-259.

Russell et al., "The synthesis of 2-Oalkyl-myo-inositol 1-phosphates as competitive inhibitors of Inositol Monophosphatase," Carbohydr Res, Oct. 9, 1992, vol. 234, pp. 263-268.

Abstract of Scheele J., et al., "Chlorinated Hydrocarbons in the Bone Marrow of Children: Studies on Their Association with Leukemia," Eur J Pediatr, Nov. 1992, vol. 151, pp. 802-805.

Abstract of Scriba, GK, et al,, "Bioavailability and Anticonvulsant Activity of a Monoglyceride-Derived Product of Phenytoin After Oral Administration to Rats," J Pharm Sci, Mar. 1995, pp. 300-302, vol. 84.

Abstract of Srivastava, SP, et al., "Testicular Effects of di-n-butyl Phithalate (DBP): Biochemical and Histopathological Alterations," Arch Toxicol, 1990, pp. 148-152, vol. 64.

Abstract of Supuran, CT, et al., "Novel Aromatic/Heterocyclic Sulfonamides and Their Metal Complexes as Inhibitors of Carbonic Anhydrase Isozymes I, II, IV," J Enzyme Ihnhib. Apr. 1997, vol. 12, pp. 37-51.

Abstract of Thormar, H. et al., "Inactivation of Visna Virus and Other Enveloped Viruses by Free Fatty Acids and Monoglycerides," Ann N Y Acad Sci. Jun. 6, 1994, vol. 724, pp. 464-471.

Abstract of Utsumi, K., et al., "Cryprotective Effect of Polyols on Rat Embryos During Two-Step Freezing,", Cryobiology, Jun. 1992, vol. 29, p. 332-341.

Abstract of Walker, EM Jr., et al. "Enhanced Mobilization of Hepatic Cadmium in Mice Upon Coadministration of an N, N-Disubstituted Dithiocarbamate and An Alkyl Monoester of Dimercaptosuccinate," Res Commun Chem Pathol Pharmacol, Jan. 1992, vol. 75, pp. 121-124.

Abstract of Wang, LL, et al., "Inhibition of Listeria Monocytogenes by Fatty Acid and Monoglycerides," Appl. Environ Microbiol, Feb. 1992, vol. 58, pp. 624-629.

Abstract of Zhang, Q., et al., "The Modification of Hemoglobin by a Long Crosslinking Reagent: Bis(3,5-Dibromosalicyl) Sebacate," Biochem Biophys Res Cowman, Sep. 30, 1994, vol. 203, pp. 1463-1470.

Abstract of Zieger, MA, et al., "Injury and Protection in Split-Thickness Skin After Very Rapid Cooling and Warming," Cryobiology, Aug. 1997, vol. 35, pp. 53-69.

(56) References Cited

OTHER PUBLICATIONS

American Association of Tissue Banks: Technical Manual for Skin Banking (1992).
American Association of Tissue Banks: Technical Manual Musculoskeletal Tissues (1992).
American Association of Tissue Banks: Standards for Tissue Banking (1996).
American Association of Tissue Banks: Standards for Tissue Banking (1998).
Anderson, CryoLife Letter (2009). http://www.sec.gov/Archives/edgar/data/784199/000091406210000036/cryolife8k12110ex992.htm.
A.C.J. de Backere, "Euro Skin Bank: large scale skin-banking in Europe based on glycerol-preservation of donor skin," 20 Burns, pp. S4-S9, 1994.
Baird, J., "A Houston-area company has introduced an improved way to treat severe burns using specialty processed skin from organ donors", Houston Chronicle (Dec. 14, 1993).
Basile, "A Comparative Study of Glycerinized and Lyophilized Procine Skin in Dressings for Third-Degree Burns," 69 Plastic and Reconstructive Surgery 6, p. 969, (1982).
Beard, J., "More ways devised for skin replacement", Houston Chronicle (Mar. 21, 1994).
Ben-Bassat, Hannah, "Performance and Safety of Skin Allografts," Clinics in Dermatology, 2005, vol. 23, pp. 365-375.
Billingham et al., "The Freezing, Drying and Storage of Mammalian Skin,", J. Exp. Bio., 1952, vol. 29, pp. 454,468.
Bos et al., Arthritis & Rheumatism, 46(4):976-85 (2002).
Bravenboer et al., Arthritis Res Ther, 6:R469-R476 (2004).
Brockbank, K.G.M., et al., "Vitrification: Preservation of Cellular Implants," Topics in Tissue Engineering, 2003, Chapter 12.
Canadian Office Action dated Aug. 24, 2015 in Canadian Application No. 2,693,840.
Canadian Office Action dated Nov. 25, 2014 in Canadian Application No. 2,693,840.
Caplan et al., Clinical Orthopaedics and Related Research, 342:254-69 (1997).
Chan et al., J. Surgical Research, 108:77-84 (2002).
Chou, S.K., et al., "Development of a Novel Pressure Swing Adsorption Dehydration System for the Preservation of Dermal Tissue," Materials Science and Engineering C, 2007, vol. 27, pp. 313-324.
Crapo, Peter M., et al., "An Overview of Tissue and Whole Organ Decellularization Processes," Biomaterials, Apr. 2011, pp. 3233-3243, vol. 32, No. 12.
Declaration of Dr. Stephen Badyulak, D.V.M., Ph.D, M.D. in re Inter Partes Review of U.S. Pat. No. 9,125,971, dated Sep. 8, 2015.
De Groot, AC, et al., "Contact Allergy to Di-Isopropyl Sebacate in Zineryt Lotion," Contact Dermatitis, Oct. 1991, vol. 25, p. 260.
Dias et al, "Assessment of the behavior of human dura mater when subjected to different preserving agents", 22 Rev. Assoc. Med. Bras, pp. 175-178, vol. 22, No. 78 (1976).
*LifeNet Health v. LifeCell Corporation*, Civil Action No. 2:13-CV-486, U.S. District Court for the Eastern District of Virginia, Opinion and Order, dated Jul. 18, 2014.
Extended Search Report issued in a corresponding European Patent Application No. 08780196.5, dated Mar. 4, 2014.
Final Office Action for U.S. Appl. No. 11/826,518, dated Oct. 19, 2016, 8 pages.
Final Office Action for U.S. Appl. No. 14/068,308, dated Sep. 22, 2016, 17 pages.
Ghosh et al., "A Comparison of Methodologies for the Preparation of Human-Epideral-Dermal Composites," Annals of Plastic Surgery, vol. 39, No. 4, pp. 394-404 (1997).
Gilbert, Thomas, W. et al., "Quantification of DNA in Biologic Scaffold Materials," J. Su rg. Res. Mar. 2009, pp. 135-139, vol. 152, No. 9.
Heck et al, "Composite Skin Graft: Frozen Derman Allografts Support the Engraftment and Expansion of Autologous Epidermis", J. Trauma, Feb. 1985, vol. 25, No. 2, pp. 106-112.

Hermans, M.H.E., "Clinical Experience with Glycerol-Preserved Donor Skin Treatment in Partial Thickness Burns", Burns, 1989, vol. 15, No. 1, pp. 57-59.
Hettich et al., "The Immunogenicity of Glycerol-Preserved Donor Skin", Burns, 1994, vol. 20, Supplement 1, pp. S71-S76.
Hoekstra et al., "History of the Euro Skin Bank: the innovation of preservation technologies," 20 Burns, pp. S43-S47 (1994).
Hopkins, Richard, A., et al., Decellularization Reduces Calcification While Improving Both Durability and 1-Year Functional Results of Pulmonary Homograft Valves in Juvenile Sheep, The Journal of Thoracic and Cardiovascular Surgery, 2009, pp. 907-913, vol. 137, No. 1.
Huang, Qizhi, et al, "Use of Peracetic Acid to Sterilize Human Donor Skin for Production of Acellular Dermal Matrices for Clinical Use," Wound Rep Reg. 2004, pp. 276-287, vol. 12.
Huang, Qizhi, et al., "Banking of Non-Viable Skin Allografts using High Concentrations of Glycerol or Propylene Glycol," Cell and Tissue Banking, 2004, pp. 3-21, vol. 5.
Hunziker and Kapfinger, J Bone Joint Surg, 80-B:144-50 (1998).
Ketchedjian, ARA, et al., "Ovine Panel Reactive Antibody Assay of HLA Responsivity to Allograft Bioengineered Vascular Scaffolds," The Journal of Thoracic and Cardiovascular Surgery, 2004, pp. 159-166, vol. 129, No. 1.
Khanna, S.K. et al,, "Homograft Aortic Valve Replacement: Seven Years' Experience with Antibiotic-Treated Valves," Thorax, 1981, pp. 330-337, vol. 36.
Kreis et al, "The Use of Non-Viable Glycerol-Preserved Cadaver Combined with Widely Expanded Autografts in the Treatment of Extensive Third-Degree Burns," The Journal of Trauma, Jan. 1989, pp. 51-54, vol. 29, No. 1.
Kreis, R.W. et al., "Historical Appraisal of the Use of Skin Allografts in the Treatment of Extension Full Skin Thickness Burns at the Red Cross Hospital Burns Centre, Beverwijk, The Netherlands", Burns, 1992, vol. 18, Supplement 2, pp. S19-S22.
Kwan et al., 37th Annual Meeting, Orthopaedic Research Society, Mar. 4-7, 1991, p. 75.
Langdon et al., "Reconstitution of Structure and Cell Function in Human Skin Grafts Derived from Cryopreserved Allogeneic Dermis and Autologous Cultured Keratinocytes", The Journal of Investigative Dermatology, Nov. 1988, 91(5):478-485.
Leigh et al., "Skin Equivalents and Cultured Skin: From the Petri Dish to the Patient", Wounds: A Compendium of Clinical Research and Practice, Jul.-Aug. 1991, vol. 3, No. 4, pp. 141-148.
Levin, M.D., et al., "Soft-Tissue Handling", Techniques in Orthopaedics, 1995, vol. 10, No. 2, p. 151.
Lex et al., "The use of homologous dura mater preserved in glycerin for the treatment of incisional hernias", 77 Rev. Paul, Med., pp. 123-128, vol. 77 (1971).
Ge, Liangpeng, et al. "Chapter 13: Skin Graft Preservation," Skin Grafts—Indications, Applications and Current Research, 2011, www.intechopen.com.
"LifeCell Announces Study Find Alloderm(R) Equivalent to 'Gold Standard' in Reconstructive Burn Surgery", Business Wire (Mar. 19, 1998).
*LifeNet Health v. LifeCell Corporation*, Civil Action No, 2:13-CV-486, U.S. District Court for the Eastern District of Virginia, Opinion and Order, dated Jul. 18, 2014.
Non Final Office Action for U.S. Appl. No. 14/068,308, dated Sep. 20, 2017, 11 pages.
Mackie, David P., "The Euro Skin Bank: Development and Application of Glycerol-Preserved Allografts," J Burn Care Rehabil, Jan./Feb. 1997, pp. 57-59, vol. 18.
May et al., J Burn Care Rehabil, 12:224-8 (1991).
May, J Burn Care & Rehabilitation, 11(5):484-86 (1990).
McKay et al., "Reconstruction of Human Skin from Glycerol-Preserved Allodermis and Cultured Keratinocyte Sheets", Burns, 1994, vol. 20, No. 1, pp. S19-S22.
Muco, Mucopolysaccharides, MedlinePlus WebEntry.
Mintz, B., "Revenues in the flesh: Skin graft product's demand grows", Houston Chronicle (Feb. 12, 1977).
Moreno et al., "Contribution to the study of enzymatic activity of benzonase", J. Molecular Catalysis, vol. 69, No. 3, pp. 419-427.

(56) References Cited

OTHER PUBLICATIONS

George C. Na, "Interaction of Calf Kin Colliagen with Glycerol: Linked Function Analysis", Biochemistry, 25:967-73 (1986).
OPTIM Synthetic Glycerine—Freezing Point, The Dow Chemical Company, retrieved from www.dow.com. 2017.
Orsi et al., "Carotid Arteries in the Dog: Structure and Histophysiology", Int. J. Morphol., vol. 24, No. 2, pp. 239-244, 2006.
Parker et al., "Storage of Heart Valve Allografts in Glycerol with Subsequent Antibiotic Sterilisation," Thorax, 33:638-45 (1978).
Penkova et al., Stabilizing Effect of Glycerol on Collagen Type I Isolated from Different Species, Food Chemistry, pp. 483-487, 1999.
Petition for Inter Partes Review of U.S. Pat. No. 9,125,971 filed Sep. 8, 2015.
Pigossi et al., Brazilian Medical Affairs Journal, 17(8):263-78.
Polio et al., Journal Arthroscopic and Related Surgery, 20(8):824-30 (2004).
Proano et al., Invest Ophthalmol Vis Sci, 45:2177-81(2004).
Ravishanker et al., Burns, 2003, vol. 29, pp. 369-374.
Reichardt et al., "Extracellular Matrix Molecules and Their Receptors: Functions in Neural Development," 14 Annual Review Neuroscience 14:531-70 (1991).
Richters et al., "Morphology of Glycerol-Preserved Human Cadaver Skin", Burns, vol. 22, No. 2, pp. 113-116.
Ross, DN, "Biologic Vales. Their Performance and Prospects," Circulation, Jun. 1972, pp. 1259-1272, vol. 45, No. 6.
Schaefer et al., Biorheology, 41, 503-8 (2004).
Seddon et al., Biochimica et Biophysica Acta 1666, 105-17 (2004).
D. Michael Strong, "The US Navy Tissue Bank: 50 Years on the Cutting Edge," Cell and Tissue Banking, vol. 1, pp. 9-16 (2000).
Tugural et al., Burns, vol. 25, pp. 625-635 (1999).
Van Baare et al., "Virucidal Effect of Glycerol as Used in Donor Skin Preservation", Burns, 1994, vol. 20, No. 1, pp. S77-S80.
Van Baare, et al., "Microbiological Evaluation of Glycerolized Cadaveric Donor Skin", Transplantation, Apr. 15, 1998, vol. 65, No. 7, pp. 966-970.
Wainwright, et al., "Clinical Evaluation of an Acellular Allograft Dermal Matrix in Full-Thickness Burns", J. Burn Care & Rehabilitation, vol. 17, No. 2, pp. 124-136 (Mar.-Apr. 1996).
Wilson et al., "Acellular matrix allograpft small caliber vascular prosthesis", Trans. Am. Sog. Artif., Interns, Organs, 1990, vol. 36, pp. M340-M343.
Wilson et al., "Acellular matrix: a biomaterials approach for coronary artery bypass and heart valve replacement", Society of Thoracic Surgeons, pp. S353-S358.
Yoshinaga et al., "Protection by Trehalose of DNA from Radiation Damage," Biosci, Biotech, Biochem., 1997, 61(1): 160-161.
Zerbini et al., "Result of Replacement of Cardiac Valves by Homologous Dura Mater Valves," Chest, Jun. 1975, vol. 67, No. 6.
HBBS, Hank's Balanced Salt Solution recipe and preparation, AAT Bioquest (2017).
Office Action in U.S. Appl. No. 14/068,308 issued by USPTO dated Mar. 8, 2018.

* cited by examiner

PROCESS FOR DEVITALIZING SOFT-TISSUE ENGINEERED MEDICAL IMPLANTS, AND DEVITALIZED SOFT-TISSUE MEDICAL IMPLANTS PRODUCED

FIELD OF THE INVENTION

The invention is directed toward methodologies and apparatus for use in the preparation of devitalized soft tissue implants, i.e. essentially lacking in reproductively viable cells and/or metabolically viable cells, while preferably retaining reproductively non-viable cells and/or metabolically non-viable cells and/or large molecular weight cytoplasmic proteins including actin. These devitalized, soft-tissue implants, are produced in small and commercializable quantities and include vascular and musculoskeletal graft substitutes. These implants may be derived from tissue-engineered soft tissues, tissue products derived from animal or human donors that contain cells which contain or are devoid of valve structures useful in directing the flow of fluids through tubular vascular prostheses, and/or combinations of natural tissue products and tissue-engineered soft-tissue products. The invention includes methodologies and apparatus for producing uniform, gently processed, devitalized multiple soft tissue implants, where processing time is significantly reduced and the number of implants produced per day is increased. The devitalized grafts produced are significantly improved in long-term durability and function when used in clinical applications.

BACKGROUND OF THE INVENTION

Numerous types of vascular and musculoskeletal grail substitutes have been produced in the last four decades. Vascular graft substitutes have included large and small diameter vascular, blood carrying tubular structures, grafts containing valvular structures (vein substitutes, and heart valve substitutes) and those lacking valvular structures (artery substitutes). The materials out of which these vascular grafts have been constructed have included man-made polymers, notably Dacron and Teflon in both knitted and woven configurations, and non-man-made polymers, notably tissue engineered blood vessels such as described in U.S. Pat. Nos. 4,539,716, 4,546,500, 4,835,102; blood vessels derived from animal or human donors such as described in U.S. Pat. Nos. 4,776,853, 5,558,875, 5,855,617, 5,843,181, and 5,843,180; and connective tissue grafts as described in U.S. Patent Application No. 2001/0000804 and U.S. Pat. Nos. 6,267,786, 5,865,849, 5,902,338, 5,922,027, 5,944,755, 5,984,858, 4,801,299, and 4,776,853.

The prior art processing methods are directed to decellularizing tissue grafts, i.e. removing all cellular elements, leaving a tissue matrix free from cellular elements, and are prohibitively time consuming, easily requiring numerous days, for example anywhere from eight to twenty-one days total processing time. Such long processing times result in proteolytic degradation of the matrix structures of the processed tissues and may result in the accumulation of residuals from the various processing solutions. Over the past few decades numerous efforts have been made to manage the large demand for vascular prostheses in the treatment of vascular dysfunctions/pathologies and musculoskeletal prostheses in the treatment of orthopedic dysfunctions/pathologies. While vascular prostheses are available for clinical use, they have met with limited success due to cellular and immunological complications, and the inability to remain patent and functional. These problems are especially pronounced for small diameter prostheses, i.e. less than about 6 mm. Efforts have been directed at removing those aspects of allograft and xenograft vascular prostheses that contribute to immunological "rejection" and these efforts have focused primarily on the development of various "decellularization" processes, which require unduly burdensome incubation times and vast numbers of reagents. In addition, the methods used in the prior art dictate the use of large volumes of processing solutions which do not lend themselves to the production of acellular grafts on a commercializable scale.

SUMMARY OF THE INVENTION

The inventive process described herein produces devitalized grafts including but not limited to ligaments, tendons, menisci, cartilage, skin, pericardium, dura mater, fascia, small and large intestine, placenta, veins, arteries, and heart valves. The methodology is advantageous over prior art techniques in that processing times and conditions have been optimized and reduced. In addition, the economics of production have been dramatically improved, resulting in large numbers of uniform, non-immunogenic grafts that repopulate with physiologically competent recipient cells. The grafts' collagenous matrix is substantially free from damage and retains mid-molecular weight cytoskeletal proteins for the purpose of acting as a chemoattractant to the infiltrating cells, such that those cells that infiltrate mature into the appropriate cell type. The grafts are also substantially free from contamination including, for example, free from infectious agents.

The invention embodies the use of one or more non-denaturing agents, for example, N-lauroyl sarcosinate, to solubilize the cellular components of the tissue and leave the matrix such that it is suitable for recellularization upon implantation. The invention is directed at a process for producing devitalized, soft-tissue implants including vascular grafts, veins, arteries, heart valves, tendons, ligaments, intervertebral discs, menisci and articular cartilage where processing times and conditions have been optimized to dramatically improve the economics of production as well as to produce a graft with minimum damage to the matrix structure of the devitalized graft.

The inventive process includes a method for preparing biological material(s) for implantation into a mammalian cardiovascular system, musculoskeletal system, or soft tissue system. The process removes reproductively viable cells and/or metabolically viable cells, while preferably retaining reproductively non-viable cells and/or metabolically non-viable cells and/or large molecular weight cytoplasmic proteins including, for example, actin, constituting variability in the inventive process. By varying the extent of the devitalization process, it is possible to differentially control the recellularization of the different tissue types when implanted in different clinical applications. For example, cardiovascular tissues that have been devitalized prior to implantation, need to recellularize and retain a vital cell population to rebuild and maintain the matrix structure, but must resist calcification and fibrosis. Such tissues must also recellularize quickly. Musculoskeletal tissues (tendons for example), used in orthopedic and sports medicine applications, do not need to recellularize as quickly as cardiovascular tissues and do not need to be as metabolically active as cells in cardiovascular tissues, but do need to promote mineralization and frequently fibrogenesis. Devitalized tendons, for example, are frequently used in replacement of anterior-cruciate ligaments (ACL substitute grafts) and it is important to minimize recellularization events and maximize osteointegration of such tissues within the femoral and tibial tunnels created to promote a strong attachment of such tissues to the bones being held together by the ACL substitute grafts. Thus, musculoskeletal tissues such as devitalized tendons need to retain a different amount and composition of avital cells than cardiovascular tissues that have been devitalized. Devitalized tendons that retain non-metabolically vital cells will be slow to recellularize and the remnant cell membranes left in the tissue will tend to serve as nidi for initiating nucleation of mineral deposition (calcium phosphate salt crystals) in a manner analogous to the membrane bound matrix vesicles associated with mineralization of osteoid in the formation of bone. Therefore, tissue intended to be implanted in cardiovascular applications may be more extensively devitalized than tissue that may be utilized in musculoskeletal applications. To achieve more extensive devitalization, tissues may be exposed to a longer and/or more severe treatment with endonuclease and detergents, such as Benzonase® and N-lauroyl sarcosinate in one preferred embodiment; tissues may be processed using ion exchange resins to remove additional detergent residuals; and/or tissues may be washed more extensively. According to one aspect of the invention, the tissues produced according to these differential methods result in varied post-treatment assessments. For example, when processing the less extensively devitalized tissue, visible cells, cell cytoskeletons and membrane remnants may be viewed in the histology tests, and DNA content may be approximately 5%. In comparison, in a process employing more extensively devitalized tissue post-treatment histology tests may exhibit no cells and only residual α-actin as cytoskeleton components remaining; and the remaining DNA content may be less than 5% or even less than 0.5% in one aspect. Thus, according to one aspect of the invention, tissue (such as a musculoskeletal tissue) may be devitalized such that the tissue may have a greater tendency to recalcify and have a slower rate of recellularization after implantation. On the other hand, according to the invention, other tissue, such as cardiovascular tissue, may be more extensively devitalized to permit rapid recellularization and a substantially lower tendency to calcify.

The process provides for the production of commercializable quantities of devitalized soft tissue grafts for implantation into mammalian systems. The devitalized tissue contains cytoskeletal proteins such as actin, forming a devitalized, non-soluble matrix. The resultant matrix is comprised of collagens, elastins, hyaluronins, and proteoglycans and all or most of the proteins associated with these components. The devitalized tissue produced may be implanted into a mammalian system and recellularized in vivo, or recellularized in vitro and subsequently implanted into a mammalian system.

One embodiment of the process includes the following steps: isolating from a suitable donor a desired tissue sample of the biological material; extracting the tissue with mildly alkaline hypotonic buffered solution of an endonuclease such as BENZONASE® (a registered product of Merck KGaA, Darmstadt, Germany) and one or more non-denaturing detergents, preferably one or more anionic non-denaturing detergents; washing the tissue with sterile water that passes through a bed of hydrophobic adsorbent resin and an anion exchange resin followed by a water solution, optionally containing one or more decontaminating agents including, for example, chlorine dioxide, glycerol, isopropanol; or INACTINE™ (INACTINE™ is a trademark of VI Technologies, Inc., Massachusetts); and stored in a sealed container in a storage solution optionally including isotonic saline, glycerol and/or one or more decontaminating agents.

The invention provides a process for preparing a devitalized soft tissue graft for implantation into a mammalian system and/or commercializable quantities of devitalized, soft tissue grafts, including extracting a soft tissue sample with an extracting solution including one or more non-denaturing detergents, for example, one or more non-denaturing anionic detergents, and one or more endonucleases, for example, one or more recombinant endonucleases, to produce extracted tissue; washing the extracted tissue with water that passes through a bed of hydrophobic adsorbent resin and anion exchange resin followed by treating with a water solution of a decontaminating solution including one or more decontaminating agents to produce the devitalized soft tissue graft; and storing the devitalized soft tissue graft in a storage solution optionally comprising one or more decontaminating agents.

The invention provides a process for devitalizing soft tissue grafts that alters the matrix structure of the graft and without inhibiting subsequent recellularization of the soft tissue graft or mechanical properties either in vitro, ex vivo, or in vivo.

The invention also provides a process for preparing a devitalized soft tissue graft for implantation into a mammalian system, including inducing a pressure mediated flow of an extracting solution including one or more non-denaturing anionic detergents and one or more recombinant endonucleases, through soft tissue, to produce extracted tissue; inducing a pressure mediated flow of water through a bed of hydrophobic adsorbent resin and anion exchange resin to produce extracted tissue, and inducing a pressure mediated flow of a decontaminating solution including one or more decontaminating agents through the treated tissue to produce the devitalized soft tissue graft; and storing the devitalized soft tissue graft in a storage solution including one or more decontaminating agents. The invention provides a process where the extracting solution is recirculated through the soft tissue graft. The invention further provides a process where the rinse solution is recirculated through a bed of hydrophobic adsorbent resin and anion exchange resin. The invention also provides a process where the decontaminating solution is recirculated through the soft tissue graft.

The invention provides a process for preparing a devitalized soft tissue graft for implantation into a mammalian system, including extracting a soft tissue sample with an extracting solution comprising one or more non-denaturing anionic detergents and one or more recombinant endonucleases to produce extracted tissue; washing said extracted tissue with water passing through a bed of hydrophobic adsorbent resin and anion exchange resin to produce extracted tissue and further washing said extracted tissue with a decontaminating solution comprising one or more decontaminating agents to produce said devitalized soft tissue graft; and storing said devitalized soft tissue graft in a storage solution; wherein a devitalized soft tissue graft retaining large molecular weight proteins is produced. The invention also provides a devitalization process which does not employ a denaturing detergent.

The invention provides a process for preparing a devitalized soft tissue graft for implantation into a mammalian system, including first inducing a pressure mediated flow of an of extracting solution including one or more non-denaturing anionic detergents and one or more endonucleases, through soft tissue, to produce extracted tissue; inducing a pressure mediated flow of water to pass through a bed of hydrophobic adsorbent resin an anion exchange resin, to produce extracted tissue; inducing a pressure mediated flow of decontaminating solution optionally including one or more decontaminating agents, through said treated tissue, to produce said devitalized soft tissue graft; and storing said devitalized soft tissue graft in a storage solution.

The invention also provides a devitalization process where said extracting solution, and/or the decontaminating solution, and/or the washing solution, is recirculated through said soft tissue graft. The invention provides a devitalization process where the non-denaturing anionic detergent includes one or more detergents selected from the group consisting of N-lauroyl sarcosinate, deoxychloic acid, taurocholic, glycocholic and cholic acids. The invention also provides a devitalization process where the decontaminating solution comprises sterile endotoxin-free, water and/or water solutions of one or more decontaminating agents, where the decontaminating agents are non-reactive towards the one or more non-denaturing detergents.

The invention provides a devitalized tissue raft, including a soft tissue sample substantially free from reproductively viable and/or metabolically viable and/or cellular elements produced by the inventive process where recellularization of the devitalized tissue graft in vivo or in vitro, is enhanced by the chemoattractant properties of the residual mid-molecular weight cytoskeletal proteins. The invention further provides a devitalized tissue graft, including a soft tissue sample substantially free from reproductively viable and/or metabolically viable and/or cellular elements.

The invention also provides a devitalized soft tissue sample which is a heart valve, and where the devitalized heart valve leaflets maintain normal coaptation. The invention also provides a devitalized soft tissue sample which is a vascular conduit valved or unvalved graft which maintains native function. The invention also provides a devitalized soft tissue sample which is a tendon or ligament that maintains native elasticity and native function. The invention also provides a devitalized soft tissue sample which is a meniscus or intervertebral disc that maintains native elasticity and native function.

DETAILED DESCRIPTION OF THE PREFERRED EMBODIMENTS

Figure 1:
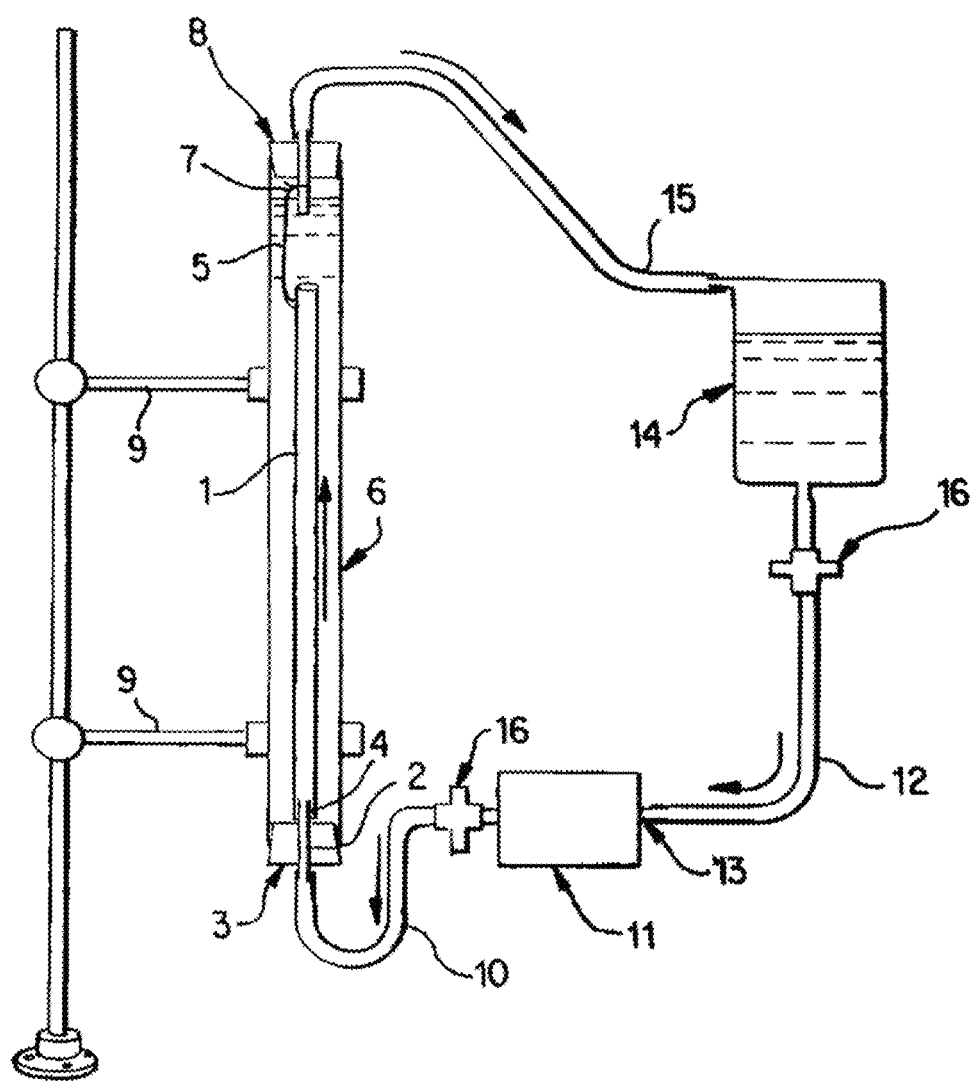
FIG. 1 illustrates a view of one embodiment of the processing chamber showing flow mediated processing of long vein segments.

Definitions.

The below definitions serve to provide a clear and consistent understanding of the specification and claims, including the scope to be given such terms.

Non-Denaturing Anionic Detergent.

By the term "non-denaturing anionic detergent" is intended for the purposes of the present invention, any detergent that does not denature protein, has a net negative charge and includes, for example, one or more detergents selected from the group consisting of N-lauroyl sarcosinate, deoxychloic acid, taurocholic, glycocholic and cholic acids.

Decontaminating Agent.

By the term "decontaminating agent" is intended for the purposes of the present invention, one or more agents which remove or inactivate/destroy any infectious material potentially present in a biological tissue sample, for example, such agents include but are not limited to one or more of the following: an antibacterial agent; an antiviral agent; an antimycotic agent; an alcohol, for example, methyl, ethyl, propyl, isopropyl, butyl, and/or t-butyl; trisodium phosphate; a preservative such as chlorine dioxide, isopropanol, METHYLPARABIN® (Croda, Inc.), INACTINE™; antimicrobials; antifungal agents; sodium hydroxide; hydrogen peroxide; a detergent; and ultrapure water, where the decontaminating agent or agents do not chemically alter the matrix components of the soft tissue grafts.

Essentially Free From.

By the term "Essentially Free From" is intended for the purposes of the present invention, a soft tissue graft where the material (for example, cellular elements and infectious materials) removed from the soft tissue graft is not detectable using detection means known in the art at the time of filing of this application.

Normal Tissue.

By the term "normal tissue" is intended for the purposes of the present invention, a particular soft tissue, for example a vein, artery, heart valve, ligament, tendon, fascia, dura mater, pericardium or skin, present in a living animal, including for example a human, a pig (porcine), a sheep (ovine), and/or a cow (bovine). Tensile properties, as well as other mechanical properties, of a particular devitalized soft tissue graft approximate, that is, are not statistically significantly different from, the tensile properties of that tissue in a living animal that are essential to the function of that tissue.

Devitalized Soft Tissue Graft.

By the term "devitalized tissue graft" it is intended for the purposes of the present invention, soft tissue including, but not limited to, veins, arteries, heart valves, ligaments, tendons, intervertebral disc, menisci, fascia, dura matter, pericardium, and skin, from any mammalian source, including but not limited to, a human source, porcine source, ovine, and a bovine source, where the devitalized graft produced is allogenic or xenogenic to the mammalian recipient, and where the devitalized tissue is essentially free from reproductively and/or metabolically viable cells, for example, a graft devoid of reproductively viable cells could contain metabolically viable cells that are incapable of increasing the numbers of metabolically viable cells through the normal process of meiosis or mitosis; a graft devoid of metabolically viable cells would, for example, be a graft devoid of cells capable of engaging in those metabolic activities essential to the normal function of those cells, i.e. the cells would be metabolically dead, a metabolically dead cell might still be visible in histology sections appearing similar to a metabolically live cell when viewed with the use of a microscope; cellular remnants, including nucleic acids, small molecular weight proteins, lipids, and polysaccharides, while the devitalized tissue retains reproductively non-viable cells and/or metabolically non-viable cells and/or large molecular weight cytoplasmic proteins, such proteins including for example, actin to act as a chemoattractant.

Non-Viable Cells:

By the term "non-viable cells" is intended for the purposes of the present invention, cells that are metabolically and/or reproductively non-viable. A metabolically non-viable cell is a cell incapable of engaging in those metabolic activities essential to the normal function of that particular cell, i.e. the cells would be metabolically dead; a metabolically dead cell might still be visible in histology sections. A reproductively non-viable cell is a cell that is incapable of increasing its numbers.

Cellular Elements:

By the term "cellular elements" is intended for the purposes of the present invention, those components including but not limited to nucleic acids, small molecular weight proteins, lipids, polysaccharides, and large molecular weight cytoplasmic proteins.

Large Molecular Weight Cytoplasmic Proteins:

By the term "large molecular weight cytoplasmic proteins" is intended for the purposes of the present invention, cellular elements that are proteins having a high molecular weight that are present in the cytoplasm of cells, such proteins preferably including those having a molecular weight of from about 50 kD to about 2 million kD, and include for example actin, desmin and vimentin.

USP Grade Sterile Water:

By the term "USP Grade Sterile Water" is intended for the purposes of the present invention, water that conforms to standards set forth in the U.S. Pharmacopia for sterility and chemical composition. Using solutions of high ionic concentration may result in the precipitation of solubilized cell remnants that may impart a tendency to the graft to be immunogenetic and or act as a nidus of calcification.

Storage Solution:

By the term "storage solution" is intended for the purposes of the present invention, a solution for storing the devitalized tissue graft and includes, for example, isotonic saline and/or a decontaminating solution optionally including one or more decontaminating agents. Such solutions include, for example, solutions of chlorine dioxide, alcohol solutions, isotonic solutions, polyhydroxy compounds such as glycerol, containing one or more decontaminating agents, the decontaminating agents including, for example, low concentrations of chlorine dioxide, INACTINE™, 70% isopropanol, or peracetic acid. These solutions may also be low molecular weight, water replacing agents including, but not limited to, glycerol as detailed in U.S. Pat. No. 6,569,200, which is incorporated by reference in its entirety.

Allowash® Solution.

By the term "Allowash® solution" is intended those compositions disclosed in U.S. Pat. No. 5,556,379 incorporated herein by reference. Examples of suitable Allowash® compositions include a cleaning composition containing about 0.06 wt % polyoxyethylene-4-lauryl ether; about 0.02 wt % poly (ethylene glycol)-p-nonyl-phenyl-ether; about 0.02 wt % octylphenol-ethylene oxide and endotoxin free deionized/distilled water.

The invention provides a process for removing viable cells, cellular remnants, nucleic acids, small molecular weight proteins, lipids, and polysaccharides, while retaining metabolically non-viable and/or reproductively non-viable cells and/or retaining large molecular weight cytoplasmic proteins including for example, actin, and without resultant damage to the matrix and/or tissue structure. In one preferred aspect, the actin is left to serve as a chemoattractant and thereby attract the appropriate cell type to infiltrate the graft and repopulate it.

Preferably, the tissue thickness does not exceed about 8 mm, more preferably does not exceed about 6 mm, and most preferably does not exceed about 4 mm, such that the time intervals described herein are sufficient for the process solutions to penetrate the tissue. Processing times may be altered to accommodate thicker tissues. A quantity of endonuclease is used for a given volume of tissue, such that the quantity is sufficient to digest the DNA and RNA within that specified volume of tissue.

The invention recognizes that the mechanical strength of soft tissue graft biomaterials resides in the matrix structure of the graft. The matrix structure of these biomaterials includes collagens, elastins, mucopolysaccharides and proteoglycan components. In a preferred aspect of the invention, the devitalization process does not substantially compromise the mechanical strength of the graft. Yet, in another preferred aspect of the invention the devitalization process does not compromise the mechanical strength of the graft.

Although the description of the invention is directed primarily at processing vascular graft materials, it should be appreciated that this invention is not restricted to processing of vascular graft materials and may also be directed to processing non-vascular soft tissue grafts. Such tissue grafts include, but are not limited to, tissues such as tendons, fascia, ligaments, menisci, pericardium, intestine, skin, dura, and cartilage. Such soft tissue may be processed by one of ordinary skill in the art to which the present invention pertains by simple manipulation of the inventive processing times, without undue experimentation.

Tissue is processed according to the invention by surgically removing normal healthy tissues, for example, veins, arteries, heart valves, tendons, ligaments, intervertebral discs, menisci, articular cartilage, etc., from animals or humans. The removed tissue is then transported to a processing facility where the tissue is cleaned of extraneous matter and quickly submersed in the first processing (extracting) solution which includes hypotonic buffered solutions containing one or more endonucleases, for example BENZONASE®, and one or more non-denaturing detergents including, for example, N-lauroyl sarcosinate. Other suitable non-denaturing anionic detergents include deoxychloic acid, taurocholic, glycocholic and cholic acids. Procurement and transport of tissue is preferably carried out sterilely and is held in a sterile container on wet ice in a solution iso-osmolar to the cellular population of the tissue being procured and transported. Furthermore, antibiotics may be added to the procurement and transport solution as long as tissue and transport solution samples are acquired for initial bioburden assessment. The invention includes the use of one or more decontaminating agents including for example one or more antibiotics, anti-fungal agents or anti-mycotic agents. Other such agents may be added during processing if so desired to maintain sterility of the procured tissues.

According to an aspect of the invention, a process for preparing biological material for implantation into a mammalian cardiovascular system, musculoskeletal system, or soft tissue system, or for recellularization in vitro, is provided and includes removing cells, cellular remnants, nucleic acids, small molecular weight proteins, lipids, and polysaccharides, while retaining large molecular weight cytoplasmic/cytoskeletal components, and forms an extracellular matrix including collagens, elastins, proteoglycans, mucopolysaccharides, and large molecular weight cytoplasmic/cytoskeletal proteins. The process includes, isolating from a suitable donor a desired tissue sample of the biological material; extracting the tissue with mildly alkaline hypotonic buffered solution of one or more endonucleases, for example BENZONASE®, and one or more anionic non-denaturing detergents including for example. N-lauroyl sarcosinate. Other suitable non-denaturing detergents include deoxychloic acid, taurocholic, glycocholic and cholic acids. Thereafter, the tissue is washed with water, which is passed through a bed of hydrophobic adsorbent resin and anion exchange resin. The tissue subsequently may be exposed to a solution containing one or more decontaminating agents, such decontaminating agents including, for example, chlorine dioxide, and alcohol. The decontaminated devitalized tissue produced is then stored in a storage solution in a sealed container, the storage solution optionally containing one or more water replacement agents such as glycerol and/or decontaminating agents, such solutions including, for example, isotonic saline; solutions of chlorine dioxide; alcohol solutions; isotonic solution containing one or more decontaminating agents, the decontaminating agents including, for example, low concentrations of chlorine dioxide or 70% isopropanol or ethanol.

The invention provides for the removal of cellular components without resultant damage to the matrix structure in which the cells resided, while ensuring that the repopulation enhancing large molecular weight cytoplasmic proteins, including cytoskeletal proteins including, for example, actin, are retained to serve as a chemoattractant.

Preferably, the soft tissue sample thickness does not exceed about 4 mm such that the time intervals described herein are sufficient for the solutions to penetrate the tissue. The concentration of endonuclease utilized is based on calculations designed at achieving a sufficient quantity of endonuclease within a given volume of tissue which is sufficient to digest the DNA within that volume of tissue in a specified period of time and is not arbitrarily chosen based on volume of processing solution. The inventive process maintains the mechanical strength of the soft tissue graft biomaterials in part because the process does not detrimentally affect the integrity of the collagen matrix structure of the graft.

The invention provides for the production of soft tissue grafts, which are readily repopulated by recipient cells, post implantation, or readily repopulated in vitro. The inventors surprisingly discovered producing a devitalized tissue which retains large molecular weight cytoplasmic proteins results in enhanced repopulation of the devitalized tissue graft after implantation. The inventors have further discovered that controlling the cellular remnants and removing processing reagents and solubilizable cellular remnants enables cells to repopulate the tissue and the cells repopulating the tissue to remain non-apoptotic facilitating long-term function and synthesis of new matrix. In one aspect, in vivo or in vitro recellularization of treated tissue is controlled by managing the levels of cellular remnants left in the tissues after devitalization. In this context, cellular remnants may include cells that are incapable of dividing, cells that are incapable of maintaining metabolic function, and cells that do not retain anything except the cytoplasmic skeleton. In one embodiment, the inventors have found that for devitalized tissues that retain reproductively nonviable cells, the cells undergo apoptosis and degrade over time after being implanted. Such tissues may promote osteointegration and may be slower to recellularize compared to tissues devitalized to retain only cytoskeletal proteins. On the other hand, devitalized tissues that retain cytoplasmic proteins and a minor amount of cellular remnants will recellularize more quickly with minimal recalcification. Thus, depending on the ultimate application of the tissue to be implanted, the devitalization process may be controlled to promote or retard recellularization and to promote or retard osteointegration. Therefore, devitalized musculoskeletal tissues (tendons for example) may preferably be processed to retain reproductively/metabolically non-vital cells and cardiovascular tissues may be processed to retain cytoplasmic proteins where the musculoskeletal tissues will be implanted in sites where the cellular remnants will promote osteointegration and retard recellularization and cytoplasmic cytoskeletal proteins will not promote cartilage or bone formation and will promote recellularization.

Although the description of this invention is directed primarily at processing vascular graft materials and tendons, it should be appreciated that this invention may also be directed to processing fascia, ligaments, menisci, intervertebral discs, pericardium, skin, dura, and cartilage by simple manipulation of processing times and parameters, such manipulation may be readily determined and employed by one of ordinary skill in the art, without undue experimentation.

In the inventive process, normal healthy vessels (veins, arteries, heart valves, tendons, ligaments, fascia, pericardium, intestine, urethra, etc.) are surgically removed from animals or humans, transported to the processing facility where they are cleaned of extraneous matter and immediately submersed in an extracting solution which contains a hypotonic buffered solution containing one or more endonucleases including for example, BENZONASE®, and one or more non-denaturing detergents including, for example, N-lauroyl sarcosinate. In that most such vessels and tendons are procured at sites distant from the processing facility and that such vessels and tendons may ultimately either be cryopreserved, devitalized or cryopreserved and subsequently devitalized, procurement and transport will normally be in a sterile container on wet ice in a solution iso-osmolar to the cellular population of the tissue being procured and transported. One or more decontaminating agents, including, for example, one or more antibiotics, may be optionally employed in any step of the inventive process, to maintain sterility of the procured tissues.

FIG. 1 illustrates the processing of a long vein grafts (1), the distal end of the vein is cannulated onto the ribbed attachment (2) of the inlet port (3) and a single suture (4) is used to secure the vein. An additional suture line (5) is attached to the proximal end of the vein for later use in maintaining the vein in an extended state in the processing vessel (6). The vein (1) is then removed from the extracting solution and transferred to the processing vessel (6) that has been temporarily inverted. The second suture line (5) along with the vein (1) is passed through the processing vessel (6) and secured to a point (7) on the outlet port end (8) of the processing vessel (6). Prior to closing the processing vessel, a portion of the extracting solution is gently added to the processing vessel and the inlet port (3), with attached vein (1), is then secured. The processing vessel (6) is turned such that the inlet port (3) is down and the outlet port (8) is up and the vessel (6) is attached to its support racking system via clamps (9). Sterile disposable tubing (10) is attached to the inlet port (3) and to pump tubing in a peristaltic pump (11). Further, sterile disposable tubing (12) is attached to the inflow side (13) of the peristaltic pump (11) and to the solution reservoir (14) which will contain all remaining extracting solution. Finally, sterile disposable tubing (15) is attached between the top (outlet) port (8) of the processing vessel (6) and the solution reservoir (14). Sterile, in-line, filters (16) may optionally be added at suitable positions in the fluid flow to safeguard sterility during processing. The extracting solution is pumped into, through and out of the processing vessel (6) such that flow of fluids through the luminal part of the vein tubule passes into the processing vessel (6) to affect constant solution change in the processing vessel and out through the outlet port (8) to a solution reservoir (14). By processing the vein in an inverted state, air which may be trapped in the luminal space of the vein will be induced to exit, thereby facilitating equal access of the processing solutions to the vein tissue being processed. Processing of the vein tissue with the extracting solution is preferably carried out at temperatures ranging from about 4° C. to about 42° C., preferably from about 10° C. to about 37° C., and most preferably from about 15° C. to about 25° C., for time periods ranging from about 1 hour to about 36 hours (overnight as necessary to accommodate processing scheduling of processing staff), preferably from about 6 hours to about 30 hours, and more preferably from about 12 hours to about 24 hours. The extracting solution is preferably pumped at a flow rate of from about 2 mls/min to about 200 mls/min, more preferably from about 5 mls/min to about 100 mls/min and most preferably from about 30 mls/min to about 60 mls/min. One preferred endonuclease (BENZONASE®) is optimally active between pH 6 and 10, and from 0° C. to above 42° C. (Merck literature describing product) when provided with 1-2 mM $Mg^{+2}$. Thereafter, the tissue is processed with a decontaminating water solution which passes through a bed of hydrophobic adsorbent resin and anion exchange resin optionally containing one or more decontaminating agents including, for example, chlorine dioxide. Under the optional processing procedures, only sufficient solution need be circulated through the processing vessel to affect one volume change of solution in the processing vessel. Under the processing procedures with the water, this solution should be circulated through the tissue at a temperature of from 0° C. to about 42° C., preferably from about 10° C. to about 37° C., and most preferably from about 15° to about 25° C., for a time period of at least 3 hours, preferably from about 1 to about 36 hours, and most preferably from about 3 to about 24 hours.

Following processing with the final processing solution, i.e. water or decontaminating water solution, the vein is removed from the processing vessel and transferred into storage solution, for example, glycerol, 70% isopropanol, or 0.001% to 0.005% chlorine dioxide in sterile ultrapure water/isotonic saline, and packaged in a volume of storage solution sufficient to cover the tissue preventing dehydration or stored between minus 80° C. and 4° C. This packaged graft may then be terminally sterilized, for example, using gamma irradiation, if so desired. Artery segments may be similarly processed, taking into consideration that veins have valves and the direction of flow must mimic the physiological flow of blood through the veins and their valves. Veins also generally have a smaller internal diameter than arteries, thus dictating slower flow rates with veins.

Figure 2:
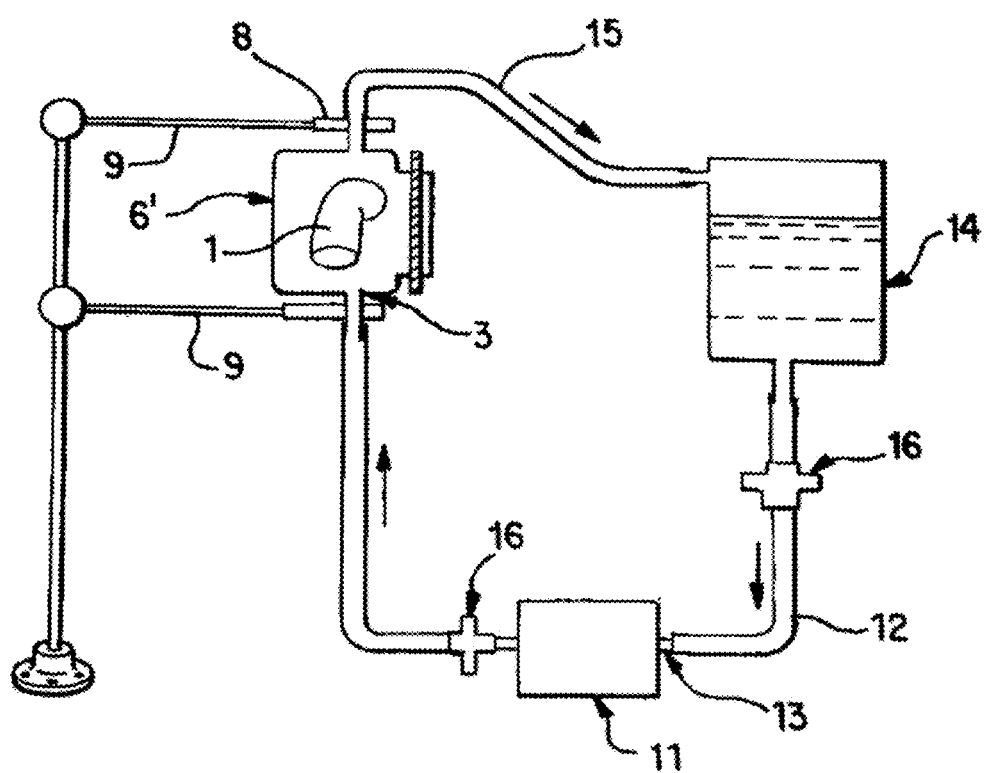
FIG. 2 illustrates a view of an embodiment of the processing chamber showing flow mediated processing of a heart valve through a deformable bag.

FIG. 2 illustrates processing heart valve grafts. The heart valve (1) is placed into the deformable processing device (6') such that the valved end of the conduit is directed towards the inlet port (3) and the non-valved end of the conduit is directed towards the outlet port (8). Prior to closing the processing vessel (6'), a portion of the extracting solution is gently added to the processing vessel. The processing vessel (6') is turned such that the inlet port (3) is down and the outlet port (8) is up to effect removal of air bubbles, and the vessel (6') is attached to its support racking system via clamps (9). Sterile disposable tubing (10) is attached to the inlet port (3) and to pump tubing in a peristaltic pump (11). Further, sterile disposable tubing (12) is attached to the inflow side (13) of the peristaltic pump (11) and to the solution reservoir (14) which will contain all remaining extracting solution. Finally, sterile disposable tubing (15) is attached between the top (outlet) port (8) of the processing vessel (6') and the solution reservoir (14). Sterile, in-line, filters (16) may optionally be added at suitable positions in the fluid flow to safeguard sterility during processing. The extracting solution is pumped into, through and out of the processing vessel (6') such that the flow of fluids through the luminal part of the heart valve (1) passes into the processing vessel (6') to affect constant solution change in the processing vessel (6') and out through the outlet port (8) to a solution reservoir (14). By processing the heart valve (1) in this orientation, air which may be trapped in the luminal space of the valve will be induced to exit facilitating equal access of the processing solutions to the valve tissue being processed. Processing of the heart valve (1) tissue with the extracting solution is performed at, for example, a temperature of from about 4° C. to about 42° C., preferably from about 10° C. to about 37° C., and most preferably from about 15° C. to about 27° C., for time periods ranging from about one hour to about 36 hours (overnight as necessary to accommodate processing scheduling of processing staff), preferably from about 6 hours to about 30 hours, and more preferably from about 12 hours to about 24 hours. The extracting solution is preferably pumped at a flow rate of from about 50 mls/min to about 350 rills/min, more preferably from about 100 mls/min to about 275 mls/min and most preferably from about 150 mls/min to about 250 mls/min. The extracting solution may be supplemented with antibiotics such as Polymixin, Vancomycin and or Lincomycin at concentrations familiar to those skilled in the art. However, Cefoxitin is inhibitory to the activity of BENZONASE® and is therefore not used to disinfect the tissue during devitalization. One preferred endonuclease, BENZONASE®, is optimally active between pH 6 and 10, and from 0° C. to above 42° C. (Merck literature describing product) when provided with 1-2 mM $Mg^2$. Following processing with the extracting solution, the extracting solution is optionally replaced with water which is recirculated through a bed of hydrophobic resin such as XAD-16® from Rohm and Haas and an anionic exchange resin, AMBERLITE 410®, from Rohm and Haas. Thereafter, the tissue is processed with a decontaminating water solution optionally containing one or more decontaminating agents including, for example, chlorine dioxide, antibiotics or isopropanol. Under the optional processing procedures, only sufficient solution (including the hypertonic salt solution) need be circulated through the processing vessel to affect one volume change of solution in the processing vessel. Under the processing procedures with water this solution should be circulated through the tissue at a temperature of from 0° C. to about 42° C., preferably from about 20° C. to about 37° C., and most preferably from about 20° C. to about 27° C., for a time period of at least three hours, preferably from about one to about twenty-four hours, and most preferably from about three to about six hours.

Following processing with the final processing solution, i.e. water or decontaminating water solution, sterile isotonic saline is circulated through the tissue such that the available volume of washing solution approximates a 1000-fold dilution of previous solutions. In this final processing step, the heart valve is removed from the processing vessel and transferred into storage solution, for example, water solution of glycerol, 70% isopropanol, or 0.001% to 0.005% chlorine dioxide in sterile ultrapure water/isotonic saline, and packaged in a volume of storage solution sufficient to cover the tissue to prevent dehydration. This packaged graft may then be terminally sterilized, for example, using gamma irradiation, if so desired.

For all other soft tissue grafts preferably the thickness does not exceed about 8 mm, more preferable does not exceed 5 mm, and most preferably the thickness does not exceed about 2-3 mm. If the thickness of the tissue graft exceeds about 5 mm, incubation and processing times need to be suitably extended. Such incubation and processing times may be readily selected and employed by one of ordinary skill in the art to which the present invention pertains without undue experimentation based on the thickness of the tissue being processed, the type of tissue being processed, and the volume of tissue being processed. Prior to closing the processing vessel, a portion of the extracting solution is gently added to the processing vessel. The vessel is attached to its support racking system, for example, via clamps. Sterile disposable tubing is attached to the inlet port and to pump tubing in a peristaltic pump. Further, sterile disposable tubing is attached to the inflow side of the peristaltic pump and to the solution reservoir, which will contain all remaining extracting solution. Finally, sterile disposable tubing is attached between the top (outlet) port of the processing vessel and the solution reservoir. Sterile, in-line, filters may optionally be added at suitable positions in the fluid flow to safeguard sterility during processing. The extracting solution is pumped into, through and out of the processing vessel such that flow of fluids occurs in close proximity to the surfaces of the soft tissue grafts into the processing vessel to affect constant solution change in the processing vessel and out through the outlet port to a solution reservoir. Processing of the soft tissue graft with the extracting solution is preferably performed at a temperature of from about 4° C. to about 42° C., preferably from about 10° C. to about 37° C., and most preferably from about 15° C. to about 27° C., for a period of time preferably of from about 1 hour to about 48 hours, (overnight as necessary to accommodate processing scheduling of processing staff), preferably from about 8 hours to about 48 hours, and more preferably from about 12 hours to about 36 hours. The extracting solution is preferably pumped at a flow rate of from about 10 mls/min to about 500 mls/min, more preferably from about 50 mls/min to about 350 mls/min and most preferably from about 100 mls/min to about 275 mls/min. One preferred endonuclease (BENZONASE®) is optimally active between pH 6 and 10, and from 0° C. to above 42° C. (Merck literature describing product) when provided with 1-2 mM $Mg^{+2}$. Following processing with the extracting solution, the rinse solution is circulated through and/or around the tissue at a temperature of from about 4° C. to about 42° C., preferably from about 10° C. to about 37° C., and most preferably from about 15° C. to about 27° C., for a time period of at least 12 hours, preferably from about 8 to about 48 hours, and most preferably from about 12 hours to 36 hours. Ultrapure sterile water is circulated through a bed of hydrophobic adsorbent resin and anion exchange resin and/or around the tissue and processing vessel. Following the water wash, the tissue is optionally processed with a decontaminating solution and a water replacement agent.

Throughout processing for all tissue grafts, the tissue is processed at a flow rate sufficient to affect a volume change in the processing vessel about every 2-5 minutes, suitable flow rates including, for example, from about 100 mls/min to about 500 mls/min, preferably from about 150 mls/min to about 300 mls/min, even more preferably from about 200 mls/min to about 250 mls/min and most preferably about 250 mls/min. Following washing with the decontaminating solution, the soft tissue graft may be removed from the processing vessel and transferred into a water replacement agent such as glycerol as a storage medium. Alternatively, the storage solutions may be pumped into the processing vessel until the decontaminating solution has been adequately exchanged and the whole processing vessel sealed, sterilized, for example, using gamma-irradiation, and used as the storage container for distribution. Suitable storage solutions are well known to those of ordinary skill in the art to which the present invention applies, and such solutions may be readily selected and employed by those of ordinary skill in the art to which the present invention applies without undue experimentation. The storage containers with solution and soft tissue grafts may be terminally sterilized using methods known in the art including, but not limited to, gamma irradiation at doses up to 2.5 Mrads.

Figure 3:
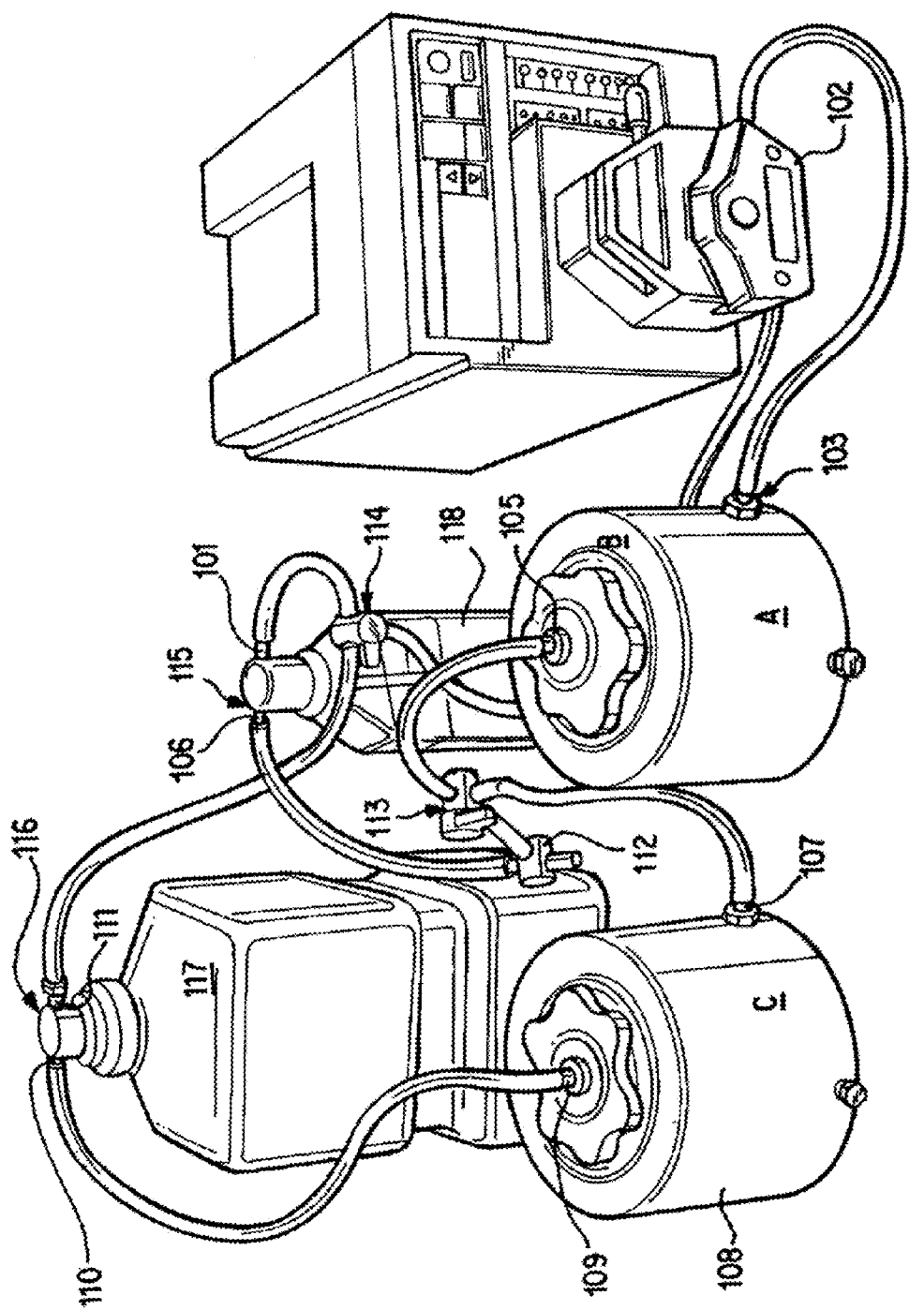
FIG. 3 illustrates a view of another embodiment of the flow-through processing chamber including a resin housing device.
Figure 4:
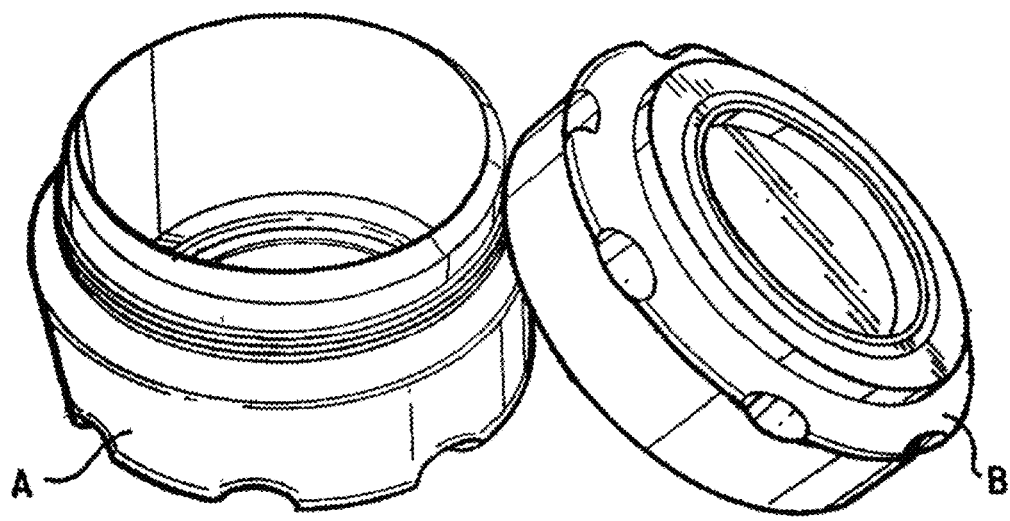
FIG. 4 illustrates a view of devitalization chamber and lid.
Figure 5:
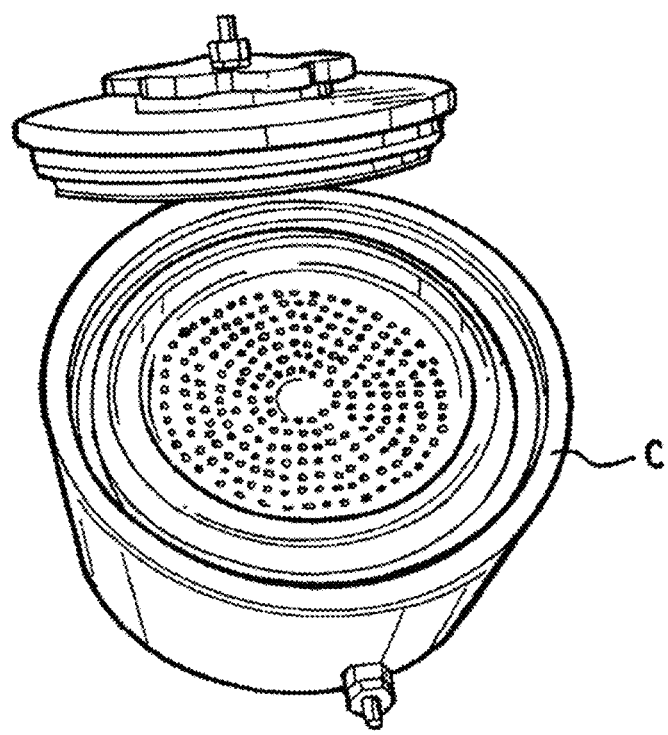
FIG. 5 illustrates a view of a resin chamber and housing.

FIG. 3 illustrates a system for processing heart valve grafts or similar non-vascular tissue grafts such as tendons. A heart valve or non-vascular tissue graft, such as a tendon, is placed into the devitalization chamber (A) using a suitable insert shown in FIG. 4 to minimize the volume processing reagents required to devitalizalize the tissue. The lid (B) is screwed down tightly to engage the o-ring thereby eliminating leakage from the chamber (A). The hydrophobic adsorbent resin and anion exchange resin are added to the resin chamber shown in FIG. 5 and placed in the resin housing (C). There is an o-ring at the top and bottom of the resin chamber to ensure a secure fit between the resin chamber and the resin housing to force the flow of water through the resin chamber. Sterile disposable tubing that is medical grade is attached to ports 101, 103, 105, 106, 107, 109 110 and 111 with 3-way stop cocks inserted in-line (112, 113, and 114). The tubing is attached to the sipper devices (115, 116) such that the return flow enters the side with the shortest spout and the outbound flow is pulled through the longest spout. The tubing is placed onto the rollers of the peristaltic pump (102) and the clamp lowered to hold the tubing in place. Once the water and devitalization solution (118) (Buffer, N-lauroyl sarcosinate, polymixin B and BENZONASE®) are connected, all connections are checked to ensure that they are tight. Pump (102) is turned on and its calibration is checked. The solution is drawn up the long spout of sipper (115) proceeds through port (101) and tubing through the roller assembly of the pump (102) into the tissue chamber through port (103) and proceeds through the insert, which diffuses the liquid through the grafts, then out the top of the chamber and through port (105) and continues past stopcocks (113 and 112) then into the sipper (115) through the short spout and port (106). This cycle continues for approximately 24 hours at 15° C. at 250 mls/minute. After the 24 hours have passed, the system is reversed to empty the tissue chamber. Stopcocks (112, 113 and 114) are turned to redirect the flow to and from the water reservoir (117) and to direct the flow through the resin housing chamber (C). The pump flow direction is then returned to the initial direction, the chamber is filled by the water exiting sipper (116) out the long spout and into the tubing through (111), through the rollers on pump (102), through the devitalization chamber (A) into the tissue chamber through port (103) and proceeds through the insert, which diffuses the liquid through the gratis, then out the top of the chamber and through port (105) and continues past stopcocks (113) which directs the flow of water into the resin housing chamber (C) through the resin chamber (108) out port (109) through the tubing and into sipper (116) via the short spout (110) and into the water reservoir (117). This cycle continues for 24 hours at 15° C. at 250 mls/minute.

When the tissue is to be removed, the pump is reversed to remove the water from the devitalization chamber and then the tissue is aseptically removed and placed into a storage solution containing 0.001% chlorine dioxide and 80% glycerol. Throughout processing for all tissue grafts, the tissue is processed at a flow rate sufficient to affect a volume change in the processing vessel about every 2-5 minutes, suitable flow rates including for example of from about 100 mls/min to about 500 mls/min, preferably from about 150 mls/min to about 300 mls/min, even more preferably from about 200 mls/min to about 250 mls/min and most preferably about 250 mls/min. Following washing with the decontaminating solution, the soft tissue van may be removed from the processing vessel and transferred into a water replacement agent such as glycerol as a storage medium. Alternatively, the storage solutions may be pumped into the processing vessel until the decontaminating solution has been adequately exchanged and the whole processing vessel sealed, sterilized for example using gamma-irradiation, and used as the storage container for distribution. Suitable storage solutions are well known to those of ordinary skill in the art to which the present invention applies, and such solutions may be readily selected and employed by those of ordinary skill in the art to which the present invention applies without undue experimentation. The storage containers with solution and soft tissue grafts may be terminally sterilized using methods known in the art including, but not limited to, gamma irradiation at doses up to 2.5 Mrads.

The following examples illustrate processing of soft tissue grafts according to the invention.

Example 1

Saphenous vein tissues (two) from each leg of an acceptable human donor were carefully dissected under sterile conditions to remove all visible fat deposits and the side vessels were tied off using non-resorbable suture materials such that the ties did not occur in close proximity to the long run of the vessel. Sutures may restrict the devitalization process and the tissues under the sutures were removed following devitalization. For long vein grafts (40-60 cm) (FIG. 1), the distal ends of the veins were cannulated onto the ribbed attachment of the inlet ports and single sutures used to secure each vein. Additional suture lines were attached to the proximal ends of the veins. The veins were then removed from the dissecting solution (RPMI 1640, papaverine) and transferred to the processing vessel which had been temporarily inverted. The second suture line along with the vein was passed through the processing vessel and secured to a point on the outlet port end of the processing vessel. Prior to closing the processing vessel, a portion of the extracting solution was gently added to the processing vessel and the inlet port, with attached vein, was then secured. The processing vessel was then turned such that the inlet port was down and the outlet port was up and the vessel attached to its support racking system via clamps. Sterile disposable tubing was attached to the inlet port and to pump tubing in a peristaltic pump. Further, sterile disposable tubing was attached to the inflow side of the peristaltic pump and to the solution reservoir which contained all remaining extracting solution. Total extracting solution volume approximated 250 ml. Finally, sterile disposable tubing was attached between the top (outlet) port of the processing vessel and the solution reservoir. Sterile, in-line, filters were added at suitable positions in the fluid flow to safeguard sterility during processing. The extracting solution was then pumped into, through and out of the processing vessel such that flow of fluids through the luminal part of the vein tubule passed into the processing vessel to affect constant solution change in the processing vessel and out through the outlet port to a solution reservoir. By processing the vein in an inverted state, air which had been "trapped" in the luminal space of the vein was induced to exit, which facilitated equal access of the processing solutions to the vein tissue being processed. Processing of the vein tissue with the extracting solution was performed at 15° C. for 24 hours using a flow rate of the extracting solution of 50 mls/min. The extracting solution consisted of 50 mM. Tris-HCL/Tris Base (pH 8.0), 2 mM $MgCl_2$, 16 mM N-lauroyl sarcosinate, and an endonuclease (BENZONASE®) (203 U/ml). Following processing with the extracting solution, water was passed through the veins and then through a bed of hydrophobic adsorbent resin (XAD-2) and anion exchange resin (Amberlite 910) at 15° C. for 24 hours at 50 mls/min. Following the rinse step a water replacement agent, glycerol was circulated through the veins in conjunction with a decontaminating agent, 0.001% chlorine dioxide, for 3 hours at 15° C. at 50 mls/min. Fluorometry using Pico green (Molecular Probes) was used to determine the percent reduction in DNA. The average percent reduction was 99.93%+/−0.03%. In addition, H&E staining and Masson's Trichrome stain were employed to look for residual nuclei and residual cell remnants, respectively. There were no nuclear remnants seen on the H&E slides and a minimal amount of desirable cytoplasmic proteins. In addition immunohistochemistry was performed to demonstrate the absence of MHCI/II proteins and the presence of alpha smooth muscle actin.

Example 2

Saphenous vein tissues (two) from each leg of an acceptable human donor were carefully dissected under sterile conditions to remove all visible fat deposits and side vessels were tied off using nonresorbable suture materials such that the ties did not occur in close proximity to the long run of the vessel. Sutures may restrict the devitalization process and the tissues under the sutures were removed following devitalization. For long vein grafts (33 and 28 cm) (FIG. 1), the distal ends of the veins were cannulated onto the ribbed attachment of the inlet ports and single sutures used to secure each vein. Additional suture lines were attached to the proximal ends of the veins. The veins were removed from the dissecting solution (RPMI 1640, papaverin) and Polymixin B. Then the veins were cryopreserved according to current guidelines in RMPI 1640, 10% fetal calf serum, and 10% DMSO and control rate frozen at 1° C./min and held in nitrogen vapor until devitalization. Prior to devitalization the tissue was thawed and diluted using an AlloFlow® chamber (disclosed in U.S. Pat. Nos. 5,879,876 and 6,326,188, which are incorporated by reference in their entireties herein). The veins were then transferred to the processing vessel, which had been temporarily inverted. The second suture line along with the vein was passed through the processing vessel and secured to a point on the outlet port end of the processing vessel. Prior to closing the processing vessel, a portion of the extracting solution was gently added to the processing vessel and the inlet port, with attached vein, was then secured. The processing vessel was then turned such that the inlet port was down and the outlet port was up and the vessel attached to its support racking system via clamps. Sterile disposable tubing was attached to the inlet port and to pump tubing in a peristaltic pump. Further, sterile disposable tubing was attached to the inflow side of the peristaltic pump and to the solution reservoir, which contained all remaining first extracting solution. Total processing solution volume approximated 250 ml. Finally, sterile disposable tubing was attached between the top (outlet) port of the processing vessel and the solution reservoir. Sterile, in-line, filters were added at suitable positions in the fluid flow to safeguard sterility during processing. The extracting solution was pumped into, through and out of the processing vessel such that flow of fluids through the luminal part of the vein tubule passed into the processing vessel to affect constant solution change in the processing vessel and out through the outlet port to a solution reservoir. By processing the vein in an inverted state, air which had been "trapped" in the luminal space of the vein was induced to exit facilitating equal access of the processing solutions to the vein tissue being processed. Processing of the vein tissue with the extracting solution was performed at 15° C. for 8 hours using a flow rate of the extracting solution of 50 mls/min. The extracting solution consisted of 50 mM Tris-HCl/Tris Base (pH 8.3), 2 mM $MgCl_2$, 32 mM n-lauroyl sarcosinate, and an endonuclease (BENZONASE®) (406 Units/ml). Following processing with the extracting solution, the extracting solution was replaced with sterile water and was circulated through the tissue and a hydrophobic adsorbent resin (XAD-16®) and anion exchange resin (AMBERLITE 410®) at a flow rate of 50 mls/min for 16 hours. Following washing in this final processing step, the vein was removed from the processing vessel and transferred into storage solution of 80% glycerol and 0.001% chlorine dioxide in sterile ultrapure water and packaged in a volume of this solution sufficient to cover the tissue. Fluorometry using Hoechst 33528 (Sigma Aldrich Chemical Company) was used to determine the percent reduction in DNA. The average percent reduction was 99.64%+/−0.07%. In addition, H&E staining and Masson's Trichrome stain were employed to look for residual nuclei and residual cell remnants, respectively. There were no nuclear remnants seen on the H&E slides and a minimal amount of desirable cytoplasmic proteins. In addition immunohistochemistry was performed to demonstrate the absence of MHCI/II proteins and the presence of alpha smooth muscle actin.

Example 3

Internal mammary artery tissues (two) from an acceptable human donor were carefully dissected under sterile conditions to remove all visible fat deposits and side vessels were tied off using nonresorbable suture materials such that the ties did not occur in close proximity to the long run of the vessel. Sutures may restrict the devitalization process and the tissues under the sutures were removed following devitalization. For short artery grafts (11 and 8 cm) (FIG. 1), one end of each artery was cannulated onto the ribbed attachment of the inlet ports and single sutures used to secure each artery. The arteries were then removed from the dissecting solution (RPMI 1640 and papaverine) and one or more antibiotics and transferred to the processing vessel which had been temporarily inverted. Prior to closing the processing vessel, a portion of the extracting solution was gently added to the processing vessel and the inlet port, with attached artery, was then secured. At this point, the processing vessel was turned such that the inlet port was down and the outlet port was up and the vessel attached to its support racking system via clamps. Sterile disposable tubing was attached to the inlet port and to pump tubing in a peristaltic pump. Further, sterile disposable tubing was attached to the inflow side of the peristaltic pump and to the solution reservoir, which contained all remaining extracting solution. Total processing solution volume approximated 150 ml. Finally, sterile disposable tubing was attached between the top (outlet) port of the processing vessel and the solution reservoir. Sterile, in-line, filters were added at suitable positions in the fluid flow to safeguard sterility during processing. The extracting solution was pumped into, through and out of the processing vessel such that flow of fluids through the luminal part of the artery tubule passed into the processing vessel to affect constant solution change in the processing vessel and out through the outlet port to a solution reservoir. By processing the artery in an inverted state, air which had been "trapped" in the luminal space of the vein was induced to exit facilitating equal access of the processing solutions to the vein tissue being processed. Processing of the artery tissue with the extracting solution was performed at 25° C. for 24 hours using a flow rate of the extracting solution of 100 ml/min. The extracting solution consisted of 50 mM Tris-HCl (pH 8.0), 2 mM $MgCl_2$, 32 mM N-lauroyl sarcosinate, and an endonuclease (BENZONASE®) (325 Units/ml). Following processing with extracting solution, the detergent solution was then replaced with ultrapure water that was pumped through the chamber and subsequently through a bed of hydrophobic resin (XAD-4®) and anion exchange resin (AMBERLITE® 910). The processing water solution was circulated (flow rate of 100 mls/min) through the tissue at room temperature (15° C.), for a time period of 36 hours. Following processing with the second processing solution, the artery was removed from the processing vessel and transferred into storage solution of 70% (v:v) pharmaceutical grade isopropanol in sterile ultra-pure water and packaged in a volume of this solution sufficient to cover the tissue. Fluorometry using Pico green (Molecular Probes) was used to determine the percent reduction in DNA. The average percent reduction was 99.23%+/−0.04%. In addition, H&E staining and Masson's Trichrome stain were employed to look for residual nuclei and residual cell remnants, respectively. There were no nuclear remnants seen on the H&E slides and a minimal amount of desirable cytoplasmic proteins. In addition immunohistochemistry was performed to demonstrate the absence of MHCI/II proteins and the presence of alpha smooth muscle actin.

Example 4

Aortic and pulmonary tissues (one each) from a heart of an acceptable human donor were carefully dissected under sterile conditions to remove all visible fat deposits and cardiac muscle tissue (leaving only a small but visible band of cardiac muscle tissue around the proximal end of the conduit). The valves were then removed from the dissecting solution (RPMI 1640) and placed in RPMI 1640 plus 10% fetal calf serum. Subsequently 10% DMSO was added drop-wise to the media, the bag was sealed and cryopreserved in a CryoMed chamber. The tissue was cooled at 1° C./min until −40° C. was achieved upon which time the tissue was transferred to the vapor phase of liquid nitrogen (LN2). At the time of use the tissue was removed from the vapor phase LN2, thawed and diluted using an AlloFlow® Chamber (AlloFlow is a trademark of LifeNet, Virginia Beach, Va.) as described in U.S. Pat. Nos. 5,879,876 and 6,326,188, which are incorporated by reference in their entireties herein. Next, the valves were placed in the devitalization chamber, some detergent solution was added and the chamber sealed. The hydrophobic adsorbent resin and anion exchange resin cartridge was snapped into place. The vessel was attached to its support racking system via clamps. Sterile disposable tubing was attached to the inlet port and to pump tubing in a peristaltic pump. Further, sterile disposable tubing was attached to the inflow side of the peristaltic pump and to the solution reservoir, which contained all remaining extracting solution. Total processing solution volume approximated 350 ml. Finally, sterile disposable tubing was attached between the top (outlet) port of the processing vessel and the solution reservoir. Sterile, in-line, filters were added at suitable positions in the fluid flow to safeguard sterility during processing. The extracting solution was pumped into, through and out of the processing vessel. Processing of the valve and conduit tissue with the extracting solution was performed at 25° C. for 24 hours using a flow rate of the extracting solution of 250 mls/min. The extracting solution consisted of 50 mM Tris-HCl (pH 8.0), 2 mM $MgCl_2$, 64 mM n-lauroyl sarcosinate, and an endonuclease (BENZONASE®) (375 Units/ml). Following processing with the extracting solution, the extracting solution was replaced with sterile ultrapure water (350 mls at a pump rate of 250 mls/min) being recirculated over a time period of 24 hours and through a bed of hydrophobic adsorbent resin (XAD-16) and anion exchange resin (AMBERLITE 410®). Following washing in this final processing step, the heart valves were removed from the processing vessel and transferred into storage solution of 0.05% chlorine dioxide and 90% glycerol in sterile ultrapure water and packaged in a volume of this solution sufficient to cover the tissue and stored at −80° C. Fluorometry using Pico green (Molecular Probes) was used to determine the percent reduction in DNA. The average percent reduction was 99.13%+/−0.06% for the conduit, 99.98%+/−0.02% for the leaflets and 99.1%+/−0.05 for the myocardium. In addition, H&E staining and Masson's Trichrome stain were employed to look for residual nuclei and residual cell remnants, respectively. There were no nuclear remnants seen on the H&E slides and a minimal amount of desirable cytoplasmic proteins visualized in the conduit and leaflet.

In addition, immunohistochemistry was performed to demonstrate the absence of MHCI/II proteins in the conduit, leaflet and myocardium and the presence of alpha smooth muscle actin in the conduit.

Example 5

The devitalized human arterial tissues as produced in Example 3, were stained with Mason Trichrome and histologically examined. Human saphenous veins were then decellularized using the method as taught in U.S. Pat. No. 4,776,853 (the "'853 patent"), the disclosure of which is incorporated by reference in its entirety herein. Specifically, the following extraction process steps, in accordance with the '853 patent, were employed in this Example:

1. A variety of arteries were treated: femoral, iliac, carotid, aortic.
2. The vessels were resected and cleaned of adhering connective tissues and debris prior to extraction.
3. Cleaned vessels were immediately placed into the first extraction solution called Solution A, which consisted of: 10 mM Tris.HCL and 5 mM EDTA at pH 8.0 supplemented with 50 U/ml penicillin/streptomycin combination (stock of 10,000 U/ml penicillin and 10,000 μg/ml streptomycin GIBCO) and 1 μM PMSF (phenylmethylsulfonyl fluoride—an antiproteolytic agent). Extraction was carried out with vessels enclosed in Nitex envelopes in a cylinder at 5° C., with stirring for 24 hours (range of 24 hours to 48 hours)
4. The vessels were placed into the second extraction solution, Solution B consisting of: 50 mM Tris.HCL, 1.5M KCL, and 1% Triton X-100 (a non-ionic detergent), 5 mM EDTA at pH 8.0 supplemented with 1 μM PMSF and 50 U/ml penicillin/streptomycin as in Solution A. Extraction was carried out with vessels in Nitex envelopes in a cylinder at 5° C. with stirring for 24 hours (range of 24 to 72 hours). The volume ratios of solutions A or B to tissue were a minimum of 100:1.
5. The vessels were washed three times in 100:1 volumes of either purified (Milli Q system 0.2 u) filtered water or the same water after autoclaving and then for 30 minutes to 1 hour in Hanks buffered salt solution (GIBCO) containing 10 mM Hepes buffer and 50 U/ml penicillin/streptomycin at 37° with rocking.
6. The vessels were treated enzymatically as follows: The vessels were transferred to solutions containing 0.75 mg/15 ml DNase I (Type III—Sigma) and RNase (Type 1A—Sigma) 1.25 mg/15 ml and rocked for 4 to 6 hours at 37° C.
7. The vessels were washed briefly one time in purified water for 30 minutes or transferred directly to solution C.
8. The vessels were mounted in Nitex envelopes and extracted with Solution C consisting of 50 mM TRIS.HCl at pH 9.0 with 1% SDS (sodium dodecyl sulphate) for 24 hours (range 24 to 96 hours) at ambient temperature.
9. The vessels were washed in >100:1 volumes of water or saline at least three times over 24 hours (range 24 to 96 hours).
10. The vessels were stored in either Hanks buffered salt solution with Hepes (10-25 mM) and penicillin and streptomycin or in phosphate buffered saline with the same antibody at 4° C. The penicillin and streptomycin concentration was raised to 100 U/ml and 100 μg/ml respectively.

The extraction procedure was initiated by hypotonic lysis of the tissue cells. Antibiotics were included from the onset of the process. No cell poisons, such as azide were used in this process which was initiated by the hypotonic lysis of the tissue cells. A high salt, non-ionic detergent combination was used to extract a substantial proportion of the cytoplasmic components. The high salt solution generally included a salt concentration in the range of 1 to 2 Molar of the desired salt. In accordance with this Example, the preferred salt was potassium chloride at 1 to 2 Molar, usually 1.5M. This type of salt will not precipitate in colder solutions at the higher concentrations. It is known from cultured cell work that this combination is gentle and leaves behind a cell cytoskeleton but completely permeabolizes the cell. A combined use of DNase and RNase was used under physiologic conditions to remove nuclear material, both enzymes being used together to provide an effective removal.

The veins processed according to the '853 patent (the "'853 arteries") of Example 5 were also stained with Mason Trichrome and histologically examined. Upon examination, the vein sections according to the invention (the "inventive arteries") stained minimally pink indicating the retention of large molecular weight cytoplasmic proteins in the arterial soft tissue matrix. On the other hand, the decellularized '853 arteries, did not show any trace of pink staining indicating the absence of large molecular weight cytoplasmic proteins. Both sets of tissue stained negatively for the presence of nuclei acids (no black staining) and both arteries stained positively for collagen (green). To confirm the identity of the pink staining proteins, the inventive arteries and the '853 arteries underwent immunohistochemical staining for alpha smooth muscle actin and desmin. The inventive arteries of Examples 1-4 stained weakly for the alpha smooth muscle actin and very weakly for the desmin relative to a cellular positive control. Conversely, the '853 arteries of Example 5 did not stain positively for either actin or desmin confirming the Massons' Trichrome stain.

Example 6

Pulmonary tissue procured from a sheep was processed according to the method described in Example 4. At the time of implant, the tissue was removed from the −80° C. freezers and placed in an AlloFlow® Chamber to thaw, dilute and rehydrate the graft. The graft was surgically implanted into the right ventricular outflow tract (RVOT) of a juvenile sheep and remained in vivo for 20 weeks. At explant the valve was examined and was unremarkable. The valve was sectioned into thirds, each third containing a leaflet, sinus of valsalva and conduit. The H&E staining demonstrated recellularization of the conduit, sinus of valsalva and one third of the leaflet. Alizarin Red S staining demonstrated all portions of the graft examined were free from calcification. The TUNEL assay demonstrated all portions of the graft were free from apoptosis. Immunohistochemistry (IHC) for alpha smooth muscle actin demonstrated staining in the media of the conduit as expected and somewhat into the media and adventitia as also expected. IHC for Factor VIII, a specific marker for endothelial cells demonstrated a smooth line of endothelial cells on the basement membrane of the conduit and on approximately one third of the leaflet. In situ hybridization for Type I collagen demonstrated collagen production in the conduit, indicating the recipient cells that had infiltrated the matrix and were making autologous collagen and turning over the devitalized donor matrix. The pressure gradients maintained at 18 mm Hg throughout the entire implant. These data are is representative of tissue explained from all 20 sheep implanted.

Example 7

Pulmonary tissue procured from a sheep was processed according to the method described in Example 4. At the time of implant, the tissue was removed from the −80° C. freezers and placed in an AlloFlow® Chamber to thaw, dilute and rehydrate the graft. The graft was fashioned into 2 patches and one was surgically implanted into the right ventricular outflow tract (RVOT) and the other into the descending thoracic aorta (DCA) of a juvenile sheep and remained in vivo for 20 weeks. The patches were sewn into a 2 cm defect in the vessel wall. At explant the patches were examined and the DCA patches were unremarkable and the RVOT patches had adhesions from the lung on the periadventital surface. The patches were sectioned into thirds, and each third was further sectioned into fifths. The sections were examined for interactions at the patch and native tissue junction and patch alone. The H&E staining demonstrated recellularization of the conduit on all sections examined. Alizarin Red S staining demonstrated all portions of the patch graft examined were free from calcification. The TUNEL assay demonstrated all portions of the patch graft were free from apoptosis. Immunohistochemistry (IHC) for alpha smooth muscle actin demonstrated staining in the media of the conduit as expected and somewhat into the media and adventitia as also expected. IHC for Factor VIII, a specific marker for endothelial cells demonstrated a smooth line of endothelial cells on the basement membrane of the conduit. In situ hybridization for Type I collagen demonstrated collagen production in the conduit, indicating the recipient cells that had infiltrated the matrix and were making autologous collagen and turning over the devitalized donor matrix.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims. Any references including patents cited herein are incorporated by reference herein in their entirety.

Example 8

Achilles, tibialis and gracilis tendons from an acceptable human donor were carefully dissected under sterile conditions to remove all bone, fascia and visible fat deposits. The tendons were then removed from the dissecting solution (RPMI 1640) and placed in RPMI 1640 plus 10% fetal calf serum. Subsequently 10% DMSO was added drop-wise to the media. The bag was then sealed and cryopreserved in a CryoMed chamber. The tissue was cooled at 1° C./min until −40° C. was achieved upon which time the tissue was transferred to the vapor phase of liquid nitrogen (LN2). At the time of use the tissue was removed from the vapor phase LN2, thawed and diluted using an AlloFlow® Chamber as described in U.S. Pat. Nos. 5,879,876 and 6,326,188, which are incorporated by reference in their entireties herein. Next, the tendons were placed in the devitalization chamber, some detergent solution was added and the chamber sealed. The hydrophobic adsorbent resin and anion exchange resin cartridge was snapped into place. The vessel was attached to its support racking system via clamps. Sterile disposable tubing was attached to the inlet port and to pump tubing in a peristaltic pump. Further, sterile disposable tubing was attached to the inflow side of the peristaltic pump and to the solution reservoir, which contained all remaining extracting solution. Total processing solution volume approximated 325 ml. Finally, sterile disposable tubing was attached between the top (outlet) port of the processing vessel and the solution reservoir. Sterile, in-line, filters were added at suitable positions in the fluid flow to safeguard sterility during processing. The extracting solution was pumped into, through and out of the processing vessel. Processing of the valve and conduit tissue with the extracting solution was performed at 25° C. for 6 hours using a flow rate of the extracting solution of 275 mls/min. The extracting solution consisted of 50 mM Tris-HCl (pH 8.0), 2 mM $MgCl_2$, 64 mM n-lauroyl sarcosinate, and an endonuclease (BENZONASE®) (350 Units/ml). Following processing with the extracting solution, the extracting solution was replaced with sterile ultrapure water (325 mls at a pump rate of 275 mls/min) being recirculated over a time period of 18 hours and through a bed of hydrophobic adsorbent resin (XAD-16®) and anion exchange resin (AMBERLITE 410®). Following washing in this final processing step, the tendons were removed from the processing vessel and transferred into storage solution of 0.05% chlorine dioxide and 90% glycerol in sterile ultrapure water and packaged in a volume of this solution sufficient to cover the tissue and stored at −80° C. Fluorometry using Pico green (Molecular Probes) was used to determine the percent reduction in DNA. The average percent reduction was 99.89%+/−0.2%. In addition, H&E staining and Masson's Trichrome stain were employed to look for residual nuclei and residual cell remnants, respectively. There were no nuclear remnants seen on the H&E slides, small amounts of cell membranes and a minimal amount of desirable cytoplasmic proteins visualized in the tendon.

Example 9

Gracilis tendon tissue procured from a sheep was processed according to the method described in Example 8. At the time of implant, the tissue was removed from the −80° C. freezers and placed in an AlloFlow® Chamber to thaw, dilute and rehydrate the graft. The graft was surgically implanted as anterior cruciate ligament repair in adult female sheep and remained in viva for 20 weeks. The surgery was a femoral tunnel with cross pin fixation for 10 animals and a tibial tunnel with staple fixation for 10 animals. At explant the tendon was examined and was unremarkable with respect to inflammatory changes such as fibrosis; however, the origin and insertion had calcified and incorporated into the patella. The tendon was sectioned into thirds, to examine the origin, insertion and middle of tendon. The H&E staining demonstrated recellularization of the tendon. The area of origin and insertion portions of the tendon also demonstrated osteoblasts, and areas of lamellae with osteocytes in the lacunae. Alizarin Red S staining demonstrated calcification localized to the insertion and origin pin sites within the tendons. The TUNEL assay demonstrated all portions of the graft were free from apoptosis. In situ hybridization for Type I collagen demonstrated collagen production in the tendon indicating the recipient cells that had infiltrated the tendon were making autologous collagen and turning over the devitalized donor matrix. These data are representative of tissue explanted from all 20 sheep implanted.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims. Any references including patents cited herein are incorporated by reference herein in their entirety.

What is claimed:

1. A process for preparing a devitalized soft tissue graft for implantation into a mammalian system from a soft tissue sample comprising large molecular weight cytoplasmic proteins, the process comprising subjecting the soft tissue sample to an extracting solution comprising a non-denaturing detergent in an amount effective for devitalizing the soft tissue sample without removing the large molecular weight cytoplasmic proteins from the soft tissue sample, wherein the non-denaturing detergent is n-lauroyl sarcosinate, whereby a devitalized soft tissue graft is obtained, and wherein the devitalized soft tissue graft retains the large molecular weight cytoplasmic proteins.

2. The process of claim 1, wherein the extracting solution further comprises an endonuclease.

3. The process of claim 2, wherein the endonuclease is a recombinant endonuclease.

4. The process of claim 1, wherein the extracting solution further comprises a decontaminating agent.

5. The process of claim 1, further comprising processing the devitalized soft tissue graft with ion exchange resins to remove the detergent.

6. The process of claim 1, further comprising washing the devitalized soft tissue graft.

7. The process of claim 1, wherein the process does not include deoxycholic acid or cholic acid.

8. The process of claim 1, wherein the devitalized soft tissue graft is for a cardiovascular application.

9. The process of claim 1, wherein the devitalized soft tissue graft is for a musculoskeletal application.

10. The process of claim 1, wherein the large molecular weight cytoplasmic proteins is selected from the group consisting of actin, desmin and vimentin.

\* \* \* \* \*